(12) United States Patent
Siddall et al.

(10) Patent No.: US 6,265,606 B1
(45) Date of Patent: Jul. 24, 2001

(54) BENZOIC ACID COMPOUNDS AND THEIR USE AS HERBICIDES

(75) Inventors: Thomas L. Siddall, Zionsville; Zoltan L. Benko, Indianapolis; Gail M. Garvin, Indianapolis; Johnny L. Jackson, Indianapolis; Jeffrey M. McQuiston, Indianapolis; David G. Ouse, Indianapolis; Thomas D. Thibault, Indianapolis; James A. Turner, Indianapolis; John C. Van Heertum, Indianapolis, all of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/309,123

(22) Filed: May 10, 1999

Related U.S. Application Data

(62) Division of application No. 09/081,388, filed on May 18, 1998, now Pat. No. 6,010,981.
(60) Provisional application No. 60/047,469, filed on May 23, 1997.

(51) Int. Cl.$^7$ .................. C07C 317/22; C07C 255/50; A01N 37/34; A01N 37/44; A01N 37/10
(52) U.S. Cl. .................. 562/429; 558/416; 562/429; 562/430; 504/310; 504/315; 504/318
(58) Field of Search .................. 562/429, 430; 558/416

(56) References Cited

U.S. PATENT DOCUMENTS

| | | |
|---|---|---|
| Re. 34,408 | 10/1993 | Tanaka et al. . |
| Re. 34,779 | 11/1994 | Oya et al. . |
| 4,063,925 | 12/1977 | Konotsune et al. . |
| 4,146,540 | 3/1979 | Avar et al. . |
| 4,230,481 | 10/1980 | Nishiyama et al. . |
| 4,643,757 | 2/1987 | Baba et al. . |
| 4,744,815 | 5/1988 | Baba et al. . |
| 4,885,022 | 12/1989 | Baba et al. . |
| 4,948,887 | 8/1990 | Baba et al. . |
| 5,155,258 * | 10/1992 | Kamiya et al. .......... 562/429 |

FOREIGN PATENT DOCUMENTS

| | | |
|---|---|---|
| 11-193275 | 7/1999 | (JP) . |
| WO 96/26206 | 8/1996 | (WO) . |

OTHER PUBLICATIONS

Provisional application No. 60/042,351, Z. Benko, et al., filed Mar. 24, 1997.
N. Miyaura and A. Suzuki, *Chemical Reviews*, 95, 2457–2483 (1995).
Nissan Chemical Industries, JP 63 122673, published May 26, 1988 (abstract and Japanese language and Chemical Abstracts, vol. 110(11), abstract No. 95226e, p. 706, published Mar. 13, 1989).
Nissan Chemical Industries, JP 63 122672, published May 26, 1988 (abstract and Japanese language and Chemical Abstracts, vol. 110(11), abstract No. 95225d, p. 706, published Mar. 13, 1989).
Nissan Chemical Industries, JP 63170365, published Jul. 14, 1988 (abstract).

* cited by examiner

*Primary Examiner*—Floyd D. Higel
*Assistant Examiner*—Ebenezer Sackey
(74) *Attorney, Agent, or Firm*—Craig E. Mixan; Kenneth L. Loertscher

(57) ABSTRACT

1-Alkyl-4-benzoyl-5-hydroxypyrazole compounds in which the benzoyl moiety is substituted in the 2-position with a halo, alkyl, or alkoxy group, in the 4-position with an alkylsulfonyl group, and in the 3-position with an optionally substituted phenyl group, for example, 1-(1,1-dimethylethyl)-4-(2-methyl-4-methyl-sulfonyl-3-(4-methoxyphenyl)benzoyl-5-hydroxypyrazole, were prepared and found to be useful for the control of a variety of broadleaf and grassy weeds. The compounds can be applied either preemergently or postemergently and can be used to control undesirable vegetation selectively in small grain crops and turf or non-selectively.

7 Claims, No Drawings

BENZOIC ACID COMPOUNDS AND THEIR USE AS HERBICIDES

CROSS-REFERENCE TO RELATED APPLICATIONS

This application claims the benefit of U.S. Provisional Application No. 60/047469, filed May 23, 1997 and a Div of Ser. No. 09/081,388 filed May 18, 1998 now U.S. Pat. No. 6,010,981.

BACKGROUND OF THE INVENTION

This invention relates to novel 1-alkyl-4-benzoyl-5-hydroxypyrazole compounds and to the use of these compounds as herbicides.

A number of 1-alkyl-4-benzoyl-5-hydroxypyrazole compounds and their herbicidal utility have been disclosed in the art, for example, in U.S. Pat. Nos. 4,230,481, 4,063,925, 4,643,757, 4,744,815, 4,885,022, 4,948,887, RE34,779, RE34,408, RE34,423, and PCT Application WO 96/26206, published Aug. 29, 1996. The compounds disclosed in these documents possess a variety of substituents on the benzoyl moiety. While herbicidal activity is present in these prior art compounds, it would be highly desirable to discover related compounds that are more active as herbicides, control a broader spectrum of undesirable vegetation, are more selective to major crops, have a more desirable environmental profile, or have a more desirable toxicological profile.

SUMMARY OF THE INVENTION

It has now been found that 1-(aliphatic)hydro-carbyl-4-benzoyl-5-hydroxypyrazole compounds possessing an unsubstituted or substituted phenyl substituent in the 3-position, an alkylsulfonyl substituent in the 4-position, and one of a few selected substituents in the 2-position of the benzoyl moiety are highly active as herbicides, control a broad spectrum of undesirable vegetation, are selective to major crops, have desirable environmental profiles, and have desirable toxicological profiles.

The invention includes benzoylpyrazole compounds of Formula I:

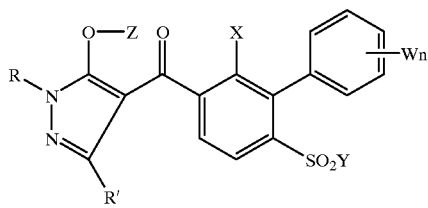

wherein
X represents F, Cl, Br, $CH_3$, $C_2H_5$, or $OCH_3$;
Y represents $CH_3$, $C_2H_5$, $CH(CH_3)_2$, or cyclo-$C_3H_5$;
Z represents H or benzyl (optionally possessing up to three ring substituents selected from F, Cl, Br, CN, $CF_3$, $NO_2$, $CH_3$, $C_2H_5$, $OCH_3$, and $OC_2H_5$);
W represents F, Cl, Br, CN, $NO_2$, OH, R", OR", OCOR", OCONHR", $OSO_2R"$, SR", SOR", $SO_2R"$, $SO_2OR"$, $SO_2NHR"$, $SO_2NR"_2$, NHR", $NR"_2$, $CO_2R"$, CONHR", or $CONR"_2$; or any two adjacent W together represent the fragment —$O(CH_2)m^O$— optionally mono to completely substituted with fluorine or methyl;
n represents 0, 1, 2, or 3;
m represents 1, 2, or 3;
R represents $C_1$–$C_4$ alkyl, $C_3$–$C_4$ alkenyl, or $C_3$–$C_4$ alkynyl;
R' represents H, $CH_2OCH_3$, or $C_1$–$C_3$ alkyl;
R" represents $C_1$–$C_4$ alkyl, $C_2$–$C_4$ alkenyl, or $C_2$–$C_4$ alkynyl each optionally mono to completely substituted with fluorine or mono substituted with Cl, Br, $O(C_1$–$C_2$ alkyl), or $S(C_1$–$C_2$ alkyl); and when Z represents H, the agriculturally acceptable salts and esters thereof.

The invention includes herbicidal compositions containing the benzoylpyrazole compounds of Formula I in combination with an agriculturally acceptable adjuvant or carrier as well as a method of use of the compounds to kill or control undesirable vegetation by application of an herbicidal amount of the compound to the vegetation or to the locus of the vegetation. The use of the compounds to kill or control weeds in rice, wheat, barley, and turf is a preferred utility and postemergence application of the compounds to the undesirable vegetation is a preferred method of application.

The invention further includes substituted benzoic acid and other intermediates that are useful in preparing the herbicidal benzoylpyrazole compounds of Formula I.

DETAILED DESCRIPTION OF THE INVENTION

The herbicidal compounds of the present invention are benzoylpyrazole compounds of Formula I:

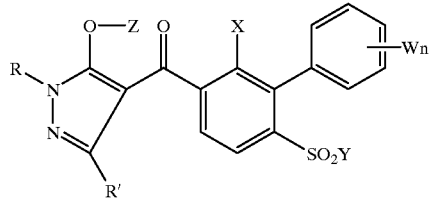

These compounds are characterized by possessing a pyrazole heterocycle moiety substituted in the 1-position with an aliphatic hydrocarbyl group and in the 5-position with an hydroxy or benzyloxy group as well as in the 4-position with a benzoyl moiety. Substitution in the 3-position of the pyrazole ring with a lower alkyl moiety is optional. The benzoyl moiety is characterized by being substituted in the 3-position with a phenyl or substituted phenyl group, in the 4-position with a lower alkylsulfonyl group, and in the 2-position with a halo, lower alkyl or lower alkoxy group. The compounds of Formula I, further, include the salt and ester compounds obtained by derivatization of the 5-position hydroxy substituent of the pyrazole moiety.

The compounds of Formula I are sometimes named as (2,3,4-trisubstituted phenyl)(1-alkyl-5-hydroxy-1H-pyrazol-4-yl)methanone compounds, but are more often referred to in the art as 1-alkyl-4-(2,3,4-trisubstituted benzoyl)-5-hydroxypyrazole compounds. The latter terminology is used herein. The compounds of Formula I wherein Z represents hydrogen are sometimes referred to as 1-alkyl-4-(2,3,4-trisubstituted benzoyl)-2-pyrazolin-5-one compounds; that is, as the keto tautomers of the formula illustrated.

The bond between the optionally substituted 3-phenyl substituent and the benzoyl moiety of the compounds of Formula I is restricted in its rotation due to steric factors and, as a result, in cases wherein the phenyl ring is asymmetrically substituted, the compounds often exist in two optical isomer forms. The definition of the compounds of the invention includes each of these isomers singly and when combined in any proportion.

The most distinguishing feature of the compounds of Formula I is the presence of the phenyl or substituted phenyl substituent in the 3-position of the benzoyl moiety. The presence of such a substituent has been found to impart unexpectedly beneficial herbicidal, environmental, and toxicological properties to benzoyl-pyrazole compounds.

Suitable substituents on the phenyl ring (W) include halo; cyano; nitro; hydroxy; optionally substituted lower alkyl, alkenyl, and alkynyl; optionally substituted lower alkoxy, alkenyloxy, and alkynyloxy; optionally substituted lower alkylcarbonyloxy, alkenylcarbonyloxy, and alkynylcarbonyloxy; optionally substituted lower alkylaminocarbonyloxy, alkenylaminocarbonyloxy, and alkynylaminocarbonyloxy; optionally substituted lower alkylsulfonyloxy, alkenylsulfonyloxy, and alkynylsulfonyloxy; optionally substituted lower alkylthio, alkenylthio, and alkynylthio; optionally substituted lower alkylsulfinyl, alkenylsulfinyl, and alkynylsulfinyl; optionally substituted lower alkylsulfonyl, alkenylsulfonyl, and alkynylsulfonyl; optionally substituted lower alkoxysulfonyl, alkenyloxysulfonyl, and alkynyloxysulfonyl; optionally substituted lower alkylaminosulfonyl, alkenylaminosulfonyl, and alkynylaminosulfonyl; optionally substituted di(lower alkyl) aminosulfonyl, alkenylaminosulfonyl, and alkynylaminosulfonyl; optionally substituted lower alkylamino, alkenylamino, and alkynylamino; optionally substituted di(lower alkyl)amino, alkenylamino, and alkynylamino; optionally substituted lower alkoxycarbonyl, alkenyloxycarbonyl, and alkynyloxycarbonyl; optionally substituted lower alkylaminocarbonyl, alkenylaminocarbonyl, and alkynylaminocarbonyl; and optionally substituted di(lower alkyl)aminocarbonyl, alkenylaminocarbonyl, and alkynylaminocarbonyl. There can be zero, one, or multiple such substituents present. In addition, any two adjacent W together can represent an optionally substituted ((poly) -methylene)dioxy fragment. The following W substituents are explicitly included in the compounds of Formula I: F, Cl, Br, CN, $NO_2$, OH, R", OR", OCOR", OCONHR", $OSO_2R$", SR", SOR", $SO_2R$", $SO_2OR$", $SO_2NHR$", $SO_2NR$"$_2$, NHR", $NR$"$_2$, $CO_2R$", CONHR", and CONR"$_2$ (wherein R" represents $C_1$–$C_4$ alkyl, $C_2$–$C_4$ alkenyl, or $C_2$–$C_4$ alkynyl each optionally mono to completely substituted with fluorine or mono substituted with Cl, Br, O($C_1$–$C_2$ alkyl), or S($C_1$–$C_2$ alkyl)) and, for any two adjacent W taken together, the fragment —O($CH_2$)$_m$O— (wherein m represents 1, 2, or 3) optionally mono to completely substituted with fluorine or methyl. Compounds wherein W represents fluoro, chloro, methyl, ethyl, hydroxy, methoxy, ethoxy, 1-methylethoxy, 2-propenyloxy (allyloxy), or methoxy-methoxy are sometimes preferred and compounds wherein W represents methoxy, ethoxy, 1-methylethoxy, or methoxy-methoxy are sometimes more preferred. Methoxy, ethoxy, and methoxymethoxy are sometimes of special interest.

The compounds of Formula I can possess zero, one, two, or three W substituents on the phenyl ring (n represents 0, 1, 2, or 3). Compounds possessing one W substituent (n represents 1) are sometimes preferred. The W substituents can be in any position on the ring. Substituents in the 4-position are often preferred. Compounds wherein Wn represents a 4-methoxy, 4-ethoxy, 4-(1-methylethoxy), or 4-methoxymethoxy substituent are generally more preferred and those wherein Wn represents a 4-methoxy, 4-ethoxy, or 4-methoxymethoxy substituent are sometimes of special interest.

The invention includes compounds of Formula I wherein the benzoyl moiety is substituted in the 4-position ($SO_2Y$) with a methylsulfonyl, ethylsulfonyl, 1-methylethylsulfonyl or cyclo-propylsulfonyl group. Methylsulfonyl groups (Y represents methyl) are typically preferred.

Compounds of Formula I substituted in the 2-position of the benzoyl moiety (X) with a halo, alkyl, or alkoxy group, such as fluoro, chloro, bromo, methyl, ethyl, and methoxy, are included in the invention. Compounds wherein X represents chloro and methyl are generally preferred and those wherein X represents methyl are usually especially preferred. Compounds wherein X and Y each represent methyl are often of special interest.

The invention includes compounds of Formula I wherein the pyrazole moiety is substituted in the 1-position (R) with an aliphatic hydrocarbyl group of 1 to 4 carbon atoms including compounds wherein R represents a $C_1$–$C_4$ alkyl, $C_3$–$C_4$ alkenyl, or $C_3$–$C_4$ alkynyl group. Compounds wherein R represents methyl, ethyl, 1-methylethyl, 1,1-dimethylethyl, or cyclo-propyl are typically preferred. Compounds wherein R represents one of methyl, ethyl, and 1,1-dimethylethyl are often independently more preferred depending on the specific herbicidal application contemplated. Compounds wherein R represents 1,1-dimethylethyl are sometimes of special interest.

Compounds of Formula I that are unsubstituted in the 3-position of the pyrazole moiety (R' represents hydrogen) or are substituted in the 3-position with methyl, ethyl, propyl, 1-methylethyl, cyclo-propyl, or methoxymethyl are included in the invention. Compounds wherein R' represents hydrogen or methyl are typically preferred and compounds wherein R' represents hydrogen are typically more preferred. Compounds wherein R represents methyl, ethyl, 1-methylethyl, 1,1-dimethyl-ethyl, or cyclo-propyl and R' represents hydrogen are often of interest.

The compounds of Formula I wherein Z represents hydrogen (5-hydroxy compounds) are believed to be the compounds that actually kill or control undesirable vegetation and are typically preferred. Analogs of such compounds that possess a derivatized hydroxy moiety which is transformed within plants or the environment to an hydroxy group possess essentially the same herbicidal effect and are within the scope of the invention. Some specifically identified derivatives within this definition include benzyl ethers (Z represents benzyl), which may be substituted with one, two, or three compatible substituents. Suitable substituents include fluoro, chloro, bromo, cyano, trifluoromethyl, nitro, methyl, ethyl, methoxy, and ethoxy. Benzyl without substituents is typically preferred.

Agriculturally acceptable salts of the compounds of Formula I, which are obtainable by treating a 5-hydroxy compound of Formula I with a base, such as a metal hydroxide, a metal carbonate, an amine, or an aminium hydroxide compound, and esters, which are obtainable by treating a 5-hydroxy compound of Formula I with an acid chloride, such as an alkanoyl chloride, a benzoyl chloride, or an alkylsulfonyl chloride, are also convertible to the hydroxy compound and are included in the invention. Amine salts are sometimes preferred forms of the compounds of Formula I because they are typically more water soluble and lend themselves more readily to the preparation of desirable aqueous based herbicidal compositions than other forms.

Compounds of Formula I wherein R represents 1,1-dimethylethyl, R' represents hydrogen, X represents methyl, Y represents methyl, and Wn represents a single 4-position substituent selected from methoxy, ethoxy, and methoxymethoxy are often highly desirable embodiments of the invention.

The terms alkyl, alkenyl, and alkynyl as used herein includes straight chain, branched chain, and cyclic hydrocarbyl moieties. Thus, typical alkyl groups are methyl, ethyl, 1-methylethyl, propyl, cyclo-propyl, 1,1-dimethylethyl, cyclo-propylmethyl, 1-methyl-cyclo-propyl, and the like. Methyl, ethyl, and 1,1-dimethylethyl are often preferred. Similarly, typical alkenyl groups include ethenyl, allyl (2-propenyl), and 1-methyl-2-propenyl and typical alkynyl groups include ethynyl and propargyl. Typical alkyl, alkenyl, and alkynyl groups mono to completely substituted with fluorine or mono substituted with Cl, Br, $O(C_1-C_2$ alkyl), or $S(C_1-C_2$ alkyl) include 2-chloroethyl, methoxymethyl, 2-methoxy-ethyl, trifluoromethyl, difluoromethyl, 1,1,2,2-tetrafluoroethyl, 2-ethylthioethyl, 3-chloroallyl, 4-methylthio-2-butynyl, 2-ethoxy-1-methylethyl, and the like.

As noted above, the invention includes the agriculturally acceptable salts and esters of compounds of Formula I wherein Z represents hydrogen, which compounds are readily transformable into compounds wherein Z represents hydrogen and which possess essentially identical herbicidal properties. The 5-position hydroxy group of the pyrazole ring of such compounds is weakly acidic and forms both salts and esters readily. Agriculturally acceptable salts and esters are defined as those salts and esters of the 5-position hydroxy group of the pyrazole ring of the compounds of Formula I (wherein Z represents hydrogen) having a cation or acid moiety that is not, itself, significantly herbicidal to any crop being treated and is not significantly deleterious to the applicator, the environment, or the ultimate user of any crop being treated.

Suitable esters include those derived from optionally substituted aliphatic and aromatic carboxylic acids, examples of which are $C_1-C_8$ alkylcarboxylic acids or $C_3-C_8$ alkenylcarboxylic acids, and benzoic acid. Suitable esters further include alkylsulfonyl esters derived from alkylsulfonic acids. $C_1-C_4$ alkanoyl and benzoyl esters are generally preferred.

Suitable cations include, for example, those derived from alkali or alkaline earth metals and those derived from ammonia and amines. Preferred cations include sodium, potassium, magnesium, and aminium cations of the formula:

$$R^5R^6R^7NH^+$$

wherein $R^5$, $R^6$, and $R^7$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups, provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as potassium hydroxide, or an amine, such as ammonia, triethylamine, dimethylamine, hydroxyethylamine, bisallylamine, 2-butoxyethylamine, morpholine, cyclododecylamine, or benzylamine.

Some independently, specifically preferred compounds of the invention include the following: 1-(1,1-dimethylethyl)-5-hydroxy-4-(2-methyl-4-methyl-sulfonyl-3-(4-methoxyphenyl)benzoyl)pyrazole, 1-ethyl-5-hydroxy-4-(2-methyl-4-methylsulfonyl-3-(4-methoxy-phenyl)benzoyl)pyrazole, 1-(1,1-dimethylethyl)-5-hydroxy-4-(2-methyl-4-methylsulfonyl-3-(4-ethoxyphenyl)benzoyl)-pyrazole, 1-(1,1-dimethylethyl)-5-hydroxy-4-(2-methyl-4-methylsulfonyl-3-(4-(methoxymethoxy)phenyl)benzoyl)-pyrazole, 1-ethyl-5-hydroxy-4-(2-methyl-4-methylsulfonyl-3-(4-(2-propenyloxy)phenyl)benzoyl)pyrazole, 1-(1,1-dimethylethyl)-5-hydroxy-4-(2-methyl-4-methylsulfonyl-3-(4-(1-methylethoxy)phenyl)benzoyl)pyrazole, and 1-(1,1-di-methylethyl)-5-hydroxy-4-(2-methyl-4-methylsulfonyl-3-(4-hydroxyphenyl)benzoyl)pyrazole.

The herbicidal compounds of the invention are exemplified by the compounds listed in Table 1.

TABLE 1

BENZOYLPYRAZOLE COMPOUNDS

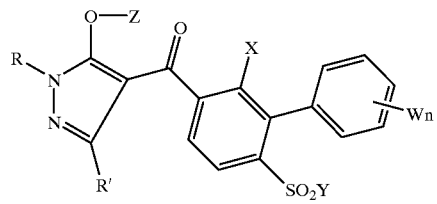

| Cpd. No. | R | R' | Z | X | Y | Wn | Form | Melting Point, °C. | Elem. Anal. Calc./Found %C | %H | %N |
|---|---|---|---|---|---|---|---|---|---|---|---|
| 1 | CH$_2$CH$_3$ | H | H | Cl | CH$_3$ | H | tan solid | 240–241 | 56.4 | 4.23 | 6.92 |
|   |   |   |   |   |   |   |   |   | 56.4 | 4.30 | 6.94 |
| 2 | C(CH$_3$)$_3$ | H | H | Cl | CH$_3$ | H | tan solid | 262.5–264 | 58.3 | 4.89 | 6.47 |
|   |   |   |   |   |   |   |   |   | 57.3 | 4.75 | 6.50 |
| 3 | CH$_2$CH$_3$ | H | H | Cl | CH$_3$ | 4-Cl | yellow solid | 240–241 | 52.0 | 3.76 | 6.38 |
|   |   |   |   |   |   |   |   |   | 51.8 | 3.52 | 6.40 |
| 4 | C(CH$_3$)$_3$ | H | H | Cl | CH$_3$ | 4-Cl | off-white solid | 256–258 | 54.0 | 4.31 | 5.99 |
|   |   |   |   |   |   |   |   |   | 53.8 | 4.31 | 5.93 |
| 5 | CH$_2$CH$_3$ | H | H | CH$_3$ | CH$_3$ | H | white solid | 151–152 | 62.5 | 5.24 | 7.30 |
|   |   |   |   |   |   |   |   |   | 62.5 | 5.32 | 7.25 |
| 6 | CH$_2$CH$_3$ | H | H | CH$_3$ | CH$_3$ | 4-CH$_3$ | white solid | 197–198 | 63.3 | 5.56 | 7.03 |
|   |   |   |   |   |   |   |   |   | 63.1 | 5.58 | 7.01 |

TABLE 1-continued

BENZOYLPYRAZOLE COMPOUNDS

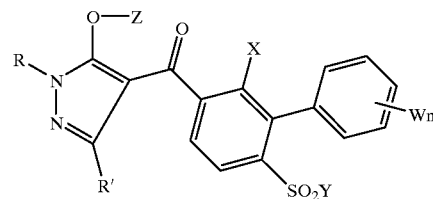

| Cpd. No. | R | R' | Z | X | Y | Wn | Form | Melting Point, °C. | %C Calc./Found | %H Calc./Found | %N Calc./Found |
|---|---|---|---|---|---|---|---|---|---|---|---|
| 7 | CH₂CH₃ | H | H | CH₃ | CH₃ | 4-CF3 | off-white solid | 155–156 | 55.8 / 55.5 | 4.23 / 4.14 | 6.19 / 6.22 |
| 8 | CH₂CH₃ | H | H | CH₃ | CH₃ | 3-CH₃ | white solid | 137.5–138.5 | 63.3 / 62.9 | 5.56 / 5.48 | 7.03 / 7.07 |
| 9 | CH₂CH₃ | H | H | CH₃ | CH₃ | 4-Cl | white solid | 209–210 | 57.4 / 57.2 | 4.57 / 4.57 | 6.69 / 6.92 |
| 10 | CH₂CH₃ | H | H | CH₃ | CH₃ | 4-OCH₃ | white solid | 146.5–147.5 | 60.9 / 60.4 | 5.35 / 5.26 | 6.76 / 7.01 |
| 11 | CH₂CH₃ | H | H | CH₃ | CH₃ | 3-Cl | white solid | 160–161 | 57.4 / 57.4 | 4.57 / 4.49 | 6.69 / 6.78 |
| 12 | CH₂CH₃ | H | H | CH₃ | CH₃ | 3,5-diCl | white solid | 185–186.5 | | | |
| 13 | CH(CH₃)₂ | H | H | CH₃ | CH₃ | 4-OCH₃ | tan solid | 174–175 | 61.7 / 61.8 | 5.64 / 5.79 | 6.54 / 5.56 |
| 14 | C(CH₃)₃ | H | H | CH₃ | CH₃ | 4-OCH₃ | white solid | 167–168 | 62.4 / 62.7 | 5.92 / 5.40 | 6.33 / 6.40 |
| 15 | CH₃ | H | H | CH₃ | CH₃ | 4-OCH₃ | tan solid | 211–212.5 | 60.5 / 59.6 | 5.03 / 4.99 | 7.00 / 7.04 |
| 16 | CH₂CH₃ | H | H | CH₃ | CH₃ | 2-CH₃ | white solid | 179–180 | 63.3 / 63.3 | 5.56 / 5.72 | 7.03 / 7.14 |
| 17 | CH₂CH₃ | H | H | CH₃ | CH₃ | 2-OCH₃ | tan solid | 181–182.5 | 60.9 / 59.7 | 5.35 / 5.45 | 6.76 / 6.90 |
| 18 | CH₂CH₃ | H | H | CH₃ | CH₃ | 2-F | lt yellow solid | 176–177 | 59.7 / 59.3 | 4.76 / 4.72 | 6.96 / 6.91 |
| 19 | CH₂CH₃ | H | H | CH₃ | CH₃ | 2-Cl | lt yellow solid | 173–174.5 | 57.4 / 57.1 | 4.57 / 4.59 | 6.69 / 6.70 |
| 20 | C(CH₃)₃ | H | H | Cl | CH₃ | 4-OCH₃ | white solid | 225–226 | 57.1 / 56.9 | 5.01 / 5.04 | 6.05 / 6.12 |
| 21 | CH₂CH₃ | H | H | CH₃ | CH₃ | 2-F, 4-OCH₃ | lt yellow solid | 151–152 | 58.3 / 57.7 | 4.89 / 4.90 | 6.43 / 6.35 |
| 22 | CH(CH₃)C₂H₅ | H | H | CH₃ | CH₃ | 4-OCH₃ | white solid | 177–178 | 62.4 / 61.9 | 5.92 / 6.04 | 6.33 / 6.38 |
| 23 | CH₂CH₃ | H | H | CH₃ | CH₃ | 2-Cl, 4-OCH₃ | lt yellow solid | 155.5–157 | 56.2 / 55.5 | 4.71 / 4.67 | 6.24 / 6.26 |
| 24 | CH₂CH₃ | H | H | CH₃ | CH₃ | 4-CN | off-white solid | 192–193 | 61.6 / 60.8 | 4.68 / 4.57 | 10.3 / 10.1 |
| 25 | CH₂CH₃ | H | H | CH₃ | CH₃ | 4-CO₂CH₃ | white solid | 159.5–160.5 | 59.7 / 59.0 | 5.01 / 5.08 | 6.33 / 6.18 |
| 26 | CH₂CH₃ | H | H | CH₃ | CH₃ | 4-OCH₂OCH₃ | yellow powder | 140–142 | 59.5 / 59.5 | 5.44 / 5.46 | 6.30 / 6.45 |
| 27 | CH₂CH₃ | H | H | CH₃ | CH₃ | 3-OCH₂OCH₃ | yellow crystals | 127–128 | 59.5 / 59.4 | 5.44 / 5.39 | 6.30 / 6.41 |
| 28 | C(CH₃)₃ | H | H | CH₃ | CH₃ | 4-OCH₂OCH₃ | golden crystals | 139–141 | 61.0 / 60.7 | 5.97 / 6.07 | 5.93 / 5.80 |
| 29 | CH₂CH₃ | H | H | CH₃ | CH₃ | 3-OCH₃ | yellow solid | 157 | 60.9 / 60.0 | 5.35 / 5.37 | 6.76 / 6.66 |
| 30 | CH₂CH₃ | H | H | CH₃ | CH₃ | 3-OCH₂CH₃ | lt yellow solid | 151 | 61.7 / 61.5 | 5.65 / 5.70 | 6.54 / 6.61 |
| 31 | CH₂CH₃ | H | H | CH₃ | CH₃ | 3-F, 4-OCH₃ | lt yellow solid | 152 | 58.3 / 58.0 | 4.89 / 4.87 | 6.48 / 6.45 |
| 32 | CH₂CH₃ | H | H | CH₃ | CH₃ | 3-Cl, 4-OCH₃ | lt yellow solid | 195 | | | |
| 33 | CH₂CH₃ | H | H | CH₃ | CH₃ | 4-OCH₂CH₃ | lt yellow solid | 164 | 61.7 / 61.6 | 5.65 / 5.62 | 6.54 / 6.54 |
| 34 | CH₂CH₃ | H | H | CH₃ | CH₃ | 3-OCH(CH₃)₂ | lt yellow solid | 165 | | | |
| 35 | CH₂CH₃ | H | H | CH₃ | CH₃ | 4-OCH(CH₃)₂ | lt yellow solid | 133 | | | |
| 36 | C(CH₃)₃ | H | H | CH₃ | CH₃ | 4-OCH₂CH₃ | white solid | 110 | | | |
| 37 | C(CH₃)₃ | H | H | CH₃ | CH₃ | 4-OCH(CH₃)₂ | lt yellow solid | 97 | | | |

TABLE 1-continued

BENZOYLPYRAZOLE COMPOUNDS

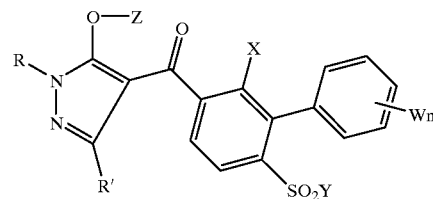

| Cpd. No. | R | R' | Z | X | Y | Wn | Form | Melting Point, °C. | % C | % H | % N |
|---|---|---|---|---|---|---|---|---|---|---|---|
| 38 | C(CH₃)₃ | H | H | CH₃ | CH₃ | 4-OCH₂CH=CH₂ | off-white powder | 108–109 | 64.1 63.8 | 6.02 6.36 | 5.98 5.93 |
| 39 | CH₂CH₃ | H | H | CH₃ | CH₃ | 3-OCF₃ | yellow solid | 74–76 | 53.8 53.9 | 4.09 4.20 | 5.98 5.94 |
| 40 | CH₂CH₃ | H | H | CH₃ | CH₃ | 4-OCF₃ | tan solid | 116–118 | 53.8 53.6 | 4.09 3.98 | 5.98 5.93 |
| 41 | CH₂CH₃ | H | H | CH₃ | CH₃ | 3-CH₃, 4-Cl | white solid | 202–204 | 58.3 58.0 | 4.89 4.77 | 6.47 6.51 |
| 42 | CH₂CH₃ | H | H | CH₃ | CH₃ | 3-Cl, 4-CH₃ | tan solid | 208–210 | 58.3 58.1 | 4.89 4.85 | 6.47 6.32 |
| 43 | CH₂CH₃ | H | H | CH₃ | CH₃ | 4-CH(CH₃)₂ | yellow solid | 155–156.5 | 64.8 64.7 | 6.14 6.11 | 6.57 6.73 |
| 44 | CH₂CH₃ | H | H | CH₃ | CH₃ | 4-CH₂CH₃ | yellow solid | 167–169 | 64.1 63.9 | 5.86 5.80 | 6.79 6.80 |
| 45 | CH₂CH₃ | H | H | CH₃ | CH₃ | 3-CH(CH₃)₂ | yellow solid | 176–178 | 64.8 64.7 | 6.14 6.12 | 6.57 6.62 |
| 46 | CH₂CH₃ | H | H | CH₃ | CH₃ | 3-CH₂CH₃ | yellow solid | 164–166 | 64.1 63.9 | 5.86 5.83 | 6.79 6.76 |
| 47 | CH₂CH₃ | H | H | CH₃ | CH₃ | 3-OCH₃, 4-Cl | tan solid | 199–205 | 56.2 56.2 | 4.72 4.71 | 6.24 6.35 |
| 48 | CH₂CH₃ | H | H | CH₃ | CH₃ | 4-F | yellow powder | 195–197 | 59.7 59.6 | 4.76 4.76 | 6.96 6.94 |
| 49 | CH₂CH₃ | H | H | CH₃ | CH₃ | 3-F | white powder | 185–187 | | | |
| 50 | CH₂CH₃ | H | H | CH₃ | CH₃ | 4-CH=CH₂ | orange powder | 179–181 | | | |
| 51 | CH₂CH₃ | H | H | CH₃ | CH₃ | 3,5-diCH₃ | yellow powder | 204–205 | | | |
| 52 | CH₂CH₃ | H | H | CH₃ | CH₃ | 3-Cl, 5-CH₃ | orange powder | 198–203 | 58.3 58.0 | 4.89 4.79 | 6.47 6.65 |
| 53 | CH₂CH₃ | H | H | CH₃ | CH₃ | 3-Cl, 4-F | yellow crystals | 128–130 | 55.0 54.9 | 4.15 4.33 | 6.41 6.36 |
| 54 | CH₂CH₃ | H | H | CH₃ | CH₃ | 3,4-diCl | off-white powder | 217–219 | 53.0 52.9 | 4.00 3.97 | 6.18 6.12 |
| 55 | CH₂CH₃ | H | H | CH₃ | CH₃ | 3,4-diOCH₃ | yellow crystals | 192–194 | 59.5 59.4 | 5.44 5.62 | 6.30 6.33 |
| 56 | CH₂CH₃ | H | H | CH₃ | CH₃ | 4-OCH₂CH₂OCH₃ | lt yellow powder | 144–146 | 60.3 60.0 | 5.72 5.67 | 6.11 6.22 |
| 57 | CH₂CH₃ | H | H | CH₃ | CH₃ | 3-OCH₂CH₂OCH₃ | yellow powder | 166–168 | 60.3 60.0 | 5.72 5.78 | 6.11 6.18 |
| 58 | C(CH₃)₃ | H | H | CH₃ | CH₃ | 3,4-diOCH₃ | lt yellow crystals | 205–207 | 61.0 60.9 | 5.97 6.66 | 5.93 5.98 |
| 59 | CH₂CH₃ | H | H | CH₃ | CH₃ | 3-CH₃, 4-OCH₃ | yellow powder | 160–161 | 61.7 61.4 | 5.65 5.74 | 6.54 6.68 |
| 60 | CH₂CH₃ | H | H | CH₃ | CH₃ | 4-OCH₂CH=CH₂ | lt yellow foam | | 62.7 62.3 | 5.49 5.46 | 6.36 6.34 |
| 61 | CH₂CH₃ | H | H | CH₃ | CH₃ | 3-OCH₂CH=CH₂ | lt yellow foam | | 62.7 62.5 | 5.49 5.57 | 6.36 6.30 |
| 62 | CH₂CH₃ | H | H | CH₃ | CH₃ | 3,4-OCH₂O— | yellow powder | 166–167 | 58.9 59.0 | 4.71 4.67 | 6.54 6.61 |
| 63 | C(CH₃)₃ | H | H | CH₃ | CH₃ | 3,4-OCH₂O— | tan powder | 218–219 | 60.5 59.1 | 5.30 5.29 | 6.14 6.09 |
| 64 | CH₂CH₃ | H | H | CH₃ | CH₃ | 3,4-OCH₂CH₂O— | tan powder | 180–181 | 59.7 59.6 | 5.01 4.96 | 6.33 6.35 |
| 65 | C(CH₃)₃ | H | H | CH₃ | CH₃ | 3,4-OCH₂CH₂O— | tan powder | 183–185 | 61.3 60.0 | 5.57 5.53 | 5.95 5.75 |
| 66 | CH₂CH₃ | H | H | CH₃ | CH₃ | 4-SO₂CH₃ | white powder | 232–233 | 54.5 54.1 | 4.79 4.92 | 6.06 5.52 |
| 67 | C(CH₃)₃ | H | H | CH₃ | CH₃ | 4-SO₂CH₃ | lt yellow powder | 187–188 | 56.3 55.8 | 5.34 5.21 | 5.71 5.59 |

TABLE 1-continued

BENZOYLPYRAZOLE COMPOUNDS

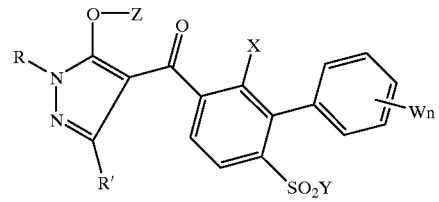

| Cpd. No. | R | R' | Z | X | Y | Wn | Form | Melting Point, °C. | Elem. Anal. Calc./Found %C | %H | %N |
|---|---|---|---|---|---|---|---|---|---|---|---|
| 68 | C(CH$_3$)$_3$ | H | H | CH$_3$ | CH$_3$ | 3-CH$_3$, 4-OCH$_3$ | yellow foam | | 63.1 / 63.1 | 6.18 / 6.22 | 6.14 / 6.06 |
| 69 | CH$_2$CH$_3$ | H | H | CH$_3$ | CH$_3$ | 4-OH | white solid | 203–205 | 60.0 / 59.7 | 5.03 / 5.04 | 7.00 / 6.93 |
| 70 | C(CH$_3$)$_3$ | H | H | CH$_3$ | CH$_3$ | 4-OH | white solid | 254–256 | 61.7 / 59.4 | 5.65 / 5.41 | 6.54 / 6.17 |
| 71 | CH$_2$CH$_3$ | H | H | CH$_3$ | CH$_3$ | 4-Br | white solid | 113–115 | 51.8 / 51.8 | 4.13 / 4.16 | 6.05 / 6.02 |
| 72 | C(CH$_3$)$_3$ | H | CH$_2$C$_6$H$_5$ | CH$_3$ | CH$_3$ | 4-OCH$_3$ | yellow glass | | 67.7 / 67.4 | 6.06 / 6.07 | 5.26 / 5.17 |
| 73 | C(CH$_3$)$_3$ | H | COCH$_3$ | CH$_3$ | CH$_3$ | 4-OCH$_3$ | white powder | 160–163 | 62.0 / 6.19 | 5.82 / 5.85 | 5.78 / 5.67 |
| 74 | CH$_2$CH$_3$ | H | H | CH$_3$ | CH$_3$ | 4-OCH$_2$CH$_2$F | white solid | 177–181 | 59.2 / 58.7 | 5.19 / 5.07 | 6.27 / 6.15 |
| 75 | C(CH$_3$)$_3$ | H | H | CH$_3$ | CH$_3$ | 4-OCH$_2$CH$_2$F | tan solid | 146–150 | | | |
| 76 | CH$_2$CH$_3$ | H | H | CH$_3$ | CH$_3$ | 4-OC(CH$_3$)$_3$ | | | | | |
| 77 | CH$_2$CH$_3$ | H | H | CH$_3$ | CH$_3$ | 4-OCH$_2$CH=CH | | | | | |
| 78 | CH$_2$CH$_3$ | H | H | CH$_3$ | CH$_3$ | 4-OCH$_2$-cyclo-C$_3$H$_5$ | | | | | |
| 79 | CH$_2$CH$_3$ | H | H | CH$_3$ | CH$_3$ | 4-CH$_2$OCH$_3$ | | | | | |
| 80 | CH$_2$CH$_3$ | H | H | CH$_3$ | CH$_3$ | 4-CON(CH$_3$)$_2$ | | | | | |
| 81 | CH$_2$CH$_3$ | H | H | CH$_3$ | CH$_3$ | 4-SO$_2$NHCH$_3$ | | | | | |
| 82 | CH$_2$CH$_3$ | H | H | CH$_3$ | CH$_3$ | 4-N(CH$_3$)$_2$ | | | | | |
| 83 | CH$_2$CH$_3$ | H | H | CH$_3$ | CH$_3$ | 4-NO$_2$ | | | | | |
| 84 | CH$_2$CH$_3$ | H | H | CH$_3$ | CH$_3$ | 3-CN | | | | | |
| 85 | CH$_2$CH$_3$ | H | H | CH$_3$ | CH$_3$ | 3-C(CH$_3$)$_3$ | | | | | |
| 86 | CH$_2$CH$_3$ | H | H | CH$_3$ | CH$_3$ | 3-SCH$_3$ | | | | | |
| 87 | C(CH$_3$)$_3$ | H | H | CH$_3$ | CH$_3$ | 3-SO$_2$CH$_3$ | | | | | |
| 88 | CH$_2$CH$_3$ | H | H | OCH$_3$ | CH$_3$ | 4-OCH$_3$ | | | | | |
| 89 | CH$_3$ | CH$_3$ | H | CH$_3$ | CH$_3$ | 4-OCHF$_{22}$ | | | | | |
| 90 | C(CH$_3$)$_3$ | H | H | CH$_3$ | CH$_3$ | 4-OC(CH$_3$)$_3$ | | | | | |
| 91 | C(CH$_3$)$_3$ | H | H | CH$_3$ | CH$_3$ | 4-C(CH$_3$)$_3$ | | | | | |
| 92 | CH$_3$ | CH$_3$ | Na | F | CH$_2$CH$_3$ | 4-CH(CH$_3$)OCH$_3$ | | | | | |
| 93 | CH(CH$_3$)$_2$ | H | COCH$_3$ | CH$_3$ | CH(CH$_3$)$_2$ | 4-OCOCH$_3$ | | | | | |
| 94 | CH(CH$_3$)$_2$ | CH$_3$ | NH$_4$ | Br | CH$_2$CH$_3$ | 4-OCONHCH$_3$ | | | | | |
| 95 | CH$_2$CH=CH | CH(CH$_3$)$_2$ | CH$_2$C$_6$H$_5$ | F | CH$_2$CH$_3$ | 4-OCH$_2$CF$_3$ | | | | | |
| 96 | cyclo-C$_3$H$_5$ | CH$_2$OCH$_3$ | (CH$_3$)$_3$NH | C$_2$H$_5$ | CH(CH$_3$)$_2$ | 4-OCH$_2$SCH$_3$ | | | | | |
| 97 | CH$_2$CH=CH$_2$ | CH$_2$CH$_3$ | SO$_2$CH$_3$ | Br | cyclo-C$_3$H$_5$ | 3,5-diCH$_3$, 4-OCH$_3$ | | | | | |
| 98 | cyclo-C$_3$H$_5$ | CH$_2$CH$_3$ | K | OCH$_3$ | CH$_3$ | 2,5-diCl, 4-OCH$_2$CH$_3$ | | | | | |

The nuclear magnetic resonance (NMR) spectra of some of the herbicidal compounds of Formula I, which spectra are completely compatible with the structures assigned to the compounds, are given in Table 2.

TABLE 2

SELECTED NMR SPECTRA

| Cpd. No. | $^1$H NMR (300 MHZ), δ ppm (from tetramethylsilane) |
|---|---|
| 5 | CDCl$_3$: 8.20 (d, 1H), 7.58 (d, 1H), 7.40 (s, 1H), 7.24 (d, 2H), 7.02 (d, 2H), 4.08 (q, 2H), 3.88 (s, 3H), 2.74 (s, 3H), 2.08 (s, 3H), 1.47 (t, 3H) |
| 12 | CDCl$_3$: 8.20 (d, 1H), 7.64 (d, 1H), 7.48 (t, 1H), 7.38 (s, 1H), 7.23 (d, 2H), 4.09 (q, 2H), 2.83 (s, 3H), 2.08 (s, 3H), 1.47 (t, 3H) |
| 14 | CDCl$_3$: 8.20 (d, 1H, J = 8.3 Hz), 7.58 (d, 1H, J = 8.3 Hz), 7.34 (s, 1H), 7.24 (d, 2H, J = 8.7 Hz), 7.02 (d, 2H, J = 8.7 Hz), 3.88 (s, 3H), 2.65 (s, 3H), 2.07 (s, 3H), 1.66 (s, 9H) |
| 17 | CDCl$_3$: 8.20 (d, 1H), 7.59 (d, 1H), 7.46 (m, 1H), 7.41 (s, 1H), 7.23 (dd, 1H), 7.10 (dd, 1H), 7.01 (d, 1H), 4.10 (q, 2H), 3.76 (s, 3H), 2.73 (s, 3H), 1.47 (t, 3H) |
| 19 | CDCl$_3$: 8.21 (d, 1H), 7.64 (d, 1H), 7.4–7.5 (m, 4H), 7.41 (s, 1H), 4.09 (q, 2H), 2.81 (s, 3H), 2.04 (s, 3H), 1.47 (t, 3H) |

TABLE 2-continued

SELECTED NMR SPECTRA

Cpd.
No. ¹H NMR (300 MHZ), δ ppm (from tetramethylsilane)

21  CDCl₃: 8.19 (d, 1H), 7.63 (d, 1H), 7.39 (s, 1H), 7.26 (d, 1H), 7.2 (d, 1H), 6.85 (dd, 1H), 6.76 (dd, 1H), 3.87 (s, 3H), 2.80 (s, 3H), 2.09 (s, 3H), 1.47 (t, 3H)
23  CDCl₃: 8.21 (d, 1H), 7.62 (d, 1H), 7.39 (s, 1H), 7.29 (d, 1H), 7.06 (d, 1H), 6.97 (dd, 1H), 3.88 (s, 3H), 2.81 (s, 3H), 2.06 s, 3H), 1.47 (t, 3H)
24  CDCl₃: 8.21 (d, 1H), 7.88 (d, 1H), 7.67 (d, 1H), 7.46 (d, 1H), 7.39 (s, 1H), 3.88 (s, 3H), 2.76 (s, 3H), 2.02 (s, 3H), 1.47 (t, 3H)
25  CDCl₃: 8.22 (d, 1H), 8.18 (d, 2H), 7.63 (d, 1H), 7.42 (d, 2H), 7.39 (s, 1H), 3.96 (s, 3H), 2.71 (s, 3H), 1.47 (t, 3H)
32  CDCl₃: 8.21 (d, 1H, J = 8.4 Hz), 7.61 (d, 1H, J = 8.4 Hz), 7.30 (m, 3H), 7.06 (d, 1H, J = 8.7 Hz), 4.09 (q, 2H, J = 7.3 Hz), 3.98 (s, 3H), 2.74 (s, 3H), 2.08 (s, 3H), 1.47 (t, 3H, J = 7.3 Hz)
34  CDCl₃: 8.21 (d, 1H, J = 8.4 Hz), 7.60 (d, 1H, J = 8.4 Hz), 7.37 (m, 2H), 6.99 (m, 1H), 6.85 (m, 2H), 4.57 (m, 1H), 4.09 (q, 3H, J = 7.3 Hz), 2.71 (s, 3H), 2.09 (s, 3H), 1.47 (t, 3H, J = 7.3 Hz), 1.35 (d, 6H, J = 6.0 Hz)
35  CDCl₃: 8.21 (d, 1H, J = 8.4 Hz), 7.58 (d, 1H, J = 8.4 Hz), 7.40 (s, 1H), 7.22 (d, 2H, J = 8.7 Hz), 6.99 (d, 2H, J = 8.7 Hz), 4.62 (m, 1H), 4.09 (q, 2H, J = 7.3 Hz), 2.65 (s, 3H), 2.08 (s, 3H), 1.47 (t, 3H, J = 7.3 Hz), 1.39 (d, 6H, J = 6.3 Hz)
36  CDCl₃: 8.20 (d, 1H, J = 8.4 Hz), 7.56 (d, 1H, J = 8.4 Hz), 7.34 (s, 1H), 7.23 (d, 2H, J = 8.7 Hz), 7.01 (d, 2H, J = 8.7 Hz), 4.10 (q, 2H, J = 7.0 Hz), 2.65 (s, 3H), 2.08 (s, 3H), 1.66 (s, 9H), 1.46 (t, 3H, J = 7.0 Hz)
37  CDCl₃: 8.20 (d, 1H, J = 8.4 Hz), 7.58 (d, 1H, J = 8.4 Hz), 7.34 (s, 1H), 7.22 (d, 2H, J = 6.6 Hz), 6.99 (d, 2H, J = 6.6 Hz), 4.63 (m, 1H), 2.65 (s, 3H), 2.09 (s, 3H), 1.67 (s, 9H), 1.40 (d, 6H, J = 6.2 Hz)
49  CDCl₃: 8.23 (d, 1H, J = 8 Hz), 7.62 (d, 1H, J = 8 Hz), 7.48 (m, 1H), 7.40 (s, 1H), 7.16 (m, 3H), 4.09 (q, 2H, J = 7 Hz), 2.74 (s, 3H), 2.06 (s, 3H), 1.47 (t, 3H, J = 7 Hz)
50  CDCl₃: 8.21 (d, 1H, J = 8.4 Hz), 7.60 (d, 1H, J = 8.4 Hz), 7.54 (d, 2H, J = 8 Hz), 7.40 (s, 1H), 7.28 (d, 2H, J = 8 Hz), 6.78 (dd, 1H, J = 17.4, 10.7 Hz), 5.86 (d, 1H, J = 17.4 Hz), 5.35 (d, 1H, J = 10.7 Hz), 4.09 (q, 2H, J = 7.3 Hz), 2.68 (s, 3H), 2.07 (s, 3H), 1.47 (t, 3H, J = 7.3 Hz)
51  CDCl₃: 8.20 (d, 1H, J = 8.0 Hz), 7.57 (d, 1H, J = 8.0 Hz), 7.39 (s, 1H), 7.09 (s, 2H), 4.09 (q, 2H, J = 7.4 Hz), 2.68 (s, 3H), 2.37 (s, 6H), 2.06 (s, 3H), 1.47 (t, 3H, J = 7 Hz)
60  CDCl₃: 8.20 (d, 1H, J = 8 Hz), 7.58 (d, 1H, J = 8 Hz), 7.40 (bs, 1H), 7.22 (d, 2H, J = 11 Hz), 7.02 (d, 2H, J = 11 Hz), 6.6 (dd, 1H, J = 5, 10, 15 Hz), 5.45 (d, 1H, J = 15 Hz), 5.32, d, 1H, J = 10 hz), 4.58 (d, 2H, J = 5 Hz), 4.08 (q, 2H, J = 5 Hz), 2.65 (s, 3H), 2.05 (s, 3H), 1.47 (t, 3H, J = 5 Hz)
70  CDCl₃: 8.20 (d, 1H, J = 8 Hz), 7.58 (d, 1H, J = 8 Hz), 7.34 (s, 1H), 7.19 (d, 2H, J = 9 Hz), 6.94 (d, 2H, J = 9 Hz), 2.69 (s, 3H), 2.08 (s, 3H), 1.67 (s, 9H)
72  CDCl₃: 8.15 (d, 1H, J = 8.3 Hz), 7.45 (m, 6H), 7.24 (m, 3H), 7.00 (m, 2H), 5.55 (s, 2H), 3.68 (s, 3H), 2.64 (s, 3H), 2.02 (s, 3H), 1.57 (s, 9H)

Compounds of Formula I can generally be prepared by the reaction of an appropriately substituted 3-phenylbenzoic acid compound of Formula II:

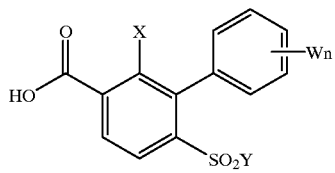

wherein X, Y, W, and n are as defined for compounds of Formula I with an appropriate 5-hydroxypyrazole compound of Formula III:

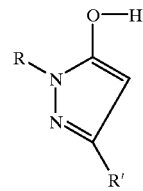

wherein R and R' are as defined for compounds of Formula I. Preparative methods that can be readily adapted for this conversion are disclosed, for example, in U.S. Pat. Nos. 4,063,925, 4,885,022, and 4,986,845. One of these methods involves the conversion of the benzoic acid compound of Formula II to its acid chloride with thionyl chloride or oxalyl chloride, the coupling of this acid chloride with a 5-hydroxypyrazole compound of Formula III in the presence of a trialkylamine compound, such as triethylamine, and the rearrangement of the originally formed ester with a base and a cyanide ion catalyst, which is typically supplied by adding acetone cyanohydrin. Another method involves the reaction of a 3-phenylbenzoic acid compound of Formula II with a 5-hydroxypyrazole compound of Formula III in the presence of 1,3-dicyclohexylcarbodiimide and the subsequent isomerization of the originally formed ester with a base and a cyanide ion catalyst, which is typically supplied by adding acetone cyanohydrin. The compounds of Formula I obtained by these procedures can be recovered using the methods exemplified herein and known in the art for related compounds.

The 3-phenylbenzoic acid compounds of Formula II can be prepared by the reaction of an appropriate 3-iodobenzoic acid compound of Formula IV:

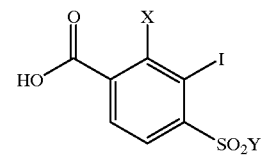

wherein X and Y are as defined for compounds of Formula I with a phenylboronic acid compound of Formula V:

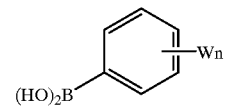

wherein W and n are as defined for compounds of Formula I, or with a substituted phenylboronic acid anhydride trimer compound derived from a phenylboronic acid compound of Formula V (an optionally substituted triphenylboroxine compound). When X represents bromo, considerable diphenylation takes place, but the desired compound is produced and can be recovered. The corresponding 3-bromobenzoic acid compounds can usually be used as well, but the results are generally not as satisfactory, especially when X represents bromo. The reaction is generally carried out by heating the reactants in an aqueous solvent, such as 1,2-dimethoxyethane, dioxane, or acetonitrile, in the presence of a base, such as potassium carbonate, and a palladium(0) catalyst, such as tetrakis(triphenylphosphine)palladium-(0) or a mixture of palladium(II) acetate and tri-o-tolylphosphine. Reactions of this type, which are generally referred to in the art as Suzuki-Miyaura reactions, are discussed in detail in *Chemical Reviews*, 95, 2457–2483 (1995). The compounds of Formula II obtained by this method can be recovered by conventional means.

3-Iodobenzoic acid compounds of Formula IV can be prepared from the corresponding 3-aminobenzoic acid compounds (3-amino-4-alkylsulfonyl-2-substituted-benzoic acid compounds) by diazotization of the 3-aminobenzoic acid compound or an ester thereof and reaction of the diazonium salt formed with iodide ion. Suitable procedures are exemplified herein and are well known in the art. 3-Amino-4-alkylsulfonyl-2-substituted-benzoic acid compounds can be prepared by amination of a corresponding 3-halobenzoic acid compound or by reduction of the corresponding 3-nitrobenzoic acid compound using methods exemplified herein and well established in the art.

2-Substituted-3-phenylbenzoic acid compounds of Formula II can also be prepared from appropriate 4-substituted-2-aminobenzothiazole compounds of Formula VI:

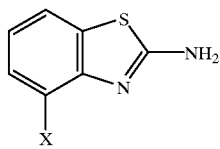

wherein X is defined as for compounds of Formula I. The method involves a sequence of chemical reactions which are individually known in the art for some of the compounds and are exemplified herein. This reaction sequence is especially useful in the preparation of compounds of Formula II wherein X represents chloro, bromo, or fluoro. The reaction sequence begins with the hydrolysis of a compound of Formula VI with a base, such as aqueous sodium hydroxide, and the alkylation of the product obtained with an alkyl halide, such as methyl iodide. The 2-substituted-6-alkylthioaniline compounds obtained can be converted into the corresponding 3-substituted-2-iodo(alkylthio)benzene compounds by diazotization and subsequent reaction of the diazonium salt formed with iodide ion under reaction conditions well established in the art for this type of reaction and exemplified herein. The 3-substituted-2-iodo(alkylthio)-benzene compounds obtained can be converted into optionally substituted 3-substituted-2-phenyl(alkylthio)-benzene compounds (2-substituted-6-alkylthiobiphenyl compounds) of Formula VII:

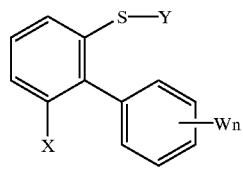

wherein X, Y, W, and n are as defined for compounds of Formula I by means of their reactions with optionally substituted phenylboronic acid compounds or substituted phenylboronic acid anhydride trimer compounds. The Suzuki-Miyaura type reaction is generally carried out as discussed hereinabove and exemplified herein; that is, by heating the reactants in an aqueous polyether solvent, such as dioxane and 1,2-dimethoxyethane or aqueous acetonitrile, in-the presence of a base, such as potassium carbonate, and a catalyst, such as tetrakis-(triphenylphosphine)palladium (0) or a mixture of palladium(II) acetate and tri-o-tolylphosphine. The optionally substituted 3-substituted-2-phenyl(alkylthio)-benzene compounds of Formula VII obtained can be converted into optionally substituted 4-bromo-3-substituted-2-phenyl(alkylsulfonyl)benzene compounds (2-substituted-3-bromo-6-alkylsulfonylbiphenyl compounds) of Formula VIII:

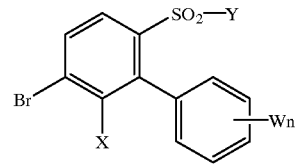

wherein X, Y, W, and n are as defined for compounds of Formula I by consecutive treatments with bromine and meta-chloroperbenzoic acid under reaction conditions exemplified herein and well known in the art for aromatic ring bromination and sulfur oxidation reactions. The compounds of Formula VIII obtained can be recovered by conventional means. Compounds of Formula VIII can be converted into optionally substituted methyl 3-phenyl-4-alkylsulfonyl-2-substituted-benzoate compounds (methyl esters of compounds of Formula II) by treatment with carbon monoxide and methanol in the presence of a trialkylamine compound, such as triethylamine, and a palladium(0) catalyst such as tetrakis(triphenyl-phosphine)palladium(0) or palladium(II) acetate and triphenylphosphine or tri-o-tolylphosphine. The reaction generally takes place at temperatures of about 80° C. to 120° C. under carbon monoxide pressure. It is generally facilitated by carbon monoxide pressures of about 200 pounds per square inch (about 14,000 kilopascals) or higher. The product methyl esters can be recovered by conventional means. Considerable dicarbonylation takes place when X represents bromo, but the desired product is formed and can be recovered. The product esters can be converted into optionally substituted 3-phenylbenzoic acid compounds of Formula II by hydrolysis using standard ester hydrolysis and acid recovery procedures well known in the art.

Phenylboronic acid compounds of Formula V can be prepared from the corresponding bromobenzene or iodobenzene compounds by lithiation of the bromobenzene or iodobenzene compound with n-butyllithium, condensation of the phenyllithium compound obtained with tri(1-methylethyl) borate (triisopropoxyborane), and hydrolysis of the phenylboronate ester product obtained with aqueous hydrochloric acid. The general procedure is well known in the art and is exemplified herein. Butyllithium is typically added to a solution of a bromobenzene compound in a solvent, such as tetrahydrofuran, under anhydrous conditions at a temperature of below −60° C. to form the corresponding phenyllithium compound and tri(1-methylethyl) borate is then added. The mixture is allowed to warm to near ambient temperature and aqueous hydrochloric acid is then added to effect the hydrolysis. Phenylboronic acid and its substituted analogs are typically soluble in organic solvents, such as ether. These compounds are sometimes recovered as the corresponding phenylboronic acid anhydride trimers instead of the acid. Phenylboronic acid compounds and their anhydride trimers are readily interconvertible and react interchangeably with iodobenzene compounds to form biphenyl compounds in Suzuki-Miyaura type reactions.

Compounds of Formula I can alternatively be prepared by the reaction of a 1-hydrocarbyl-5-hydroxy-4-(2-substituted-3-iodo-4-alkylsulfonylbenzoyl)pyrazole compound of Formula IX:

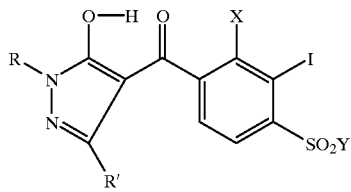

wherein R, R', X, and Y are as defined for compounds of Formula I with an optionally substituted phenylboronic acid compound of Formula V or a phenylboronic acid anhydride trimer thereof. The corresponding 3-bromobenzoylpyrazole compounds can sometimes be used as well, but the results are generally not as satisfactory, especially when X represents bromo. This Suzuki-Miyaura type reaction is generally carried out as described hereinabove and exemplified herein. A compound of Formula IX, a compound of Formula V, potassium carbonate, and a catalytic amount of tetrakis (triphenylphoshine)- palladium(0) or palladium(II) acetate and tri-o-tolylphosphine are combined in aqueous dioxane, 1,2-dimethoxyethane, or acetonitrile as a solvent and the mixture is heated at about 80° C. to 100° C. with good agitation. The compounds of Formula I prepared by this procedure can be recovered by conventional means.

Compounds of Formula IX can be prepared by the reaction of a 3-iodobenzoic acid compound of Formula IV with a 5-hydroxypyrazole compound of Formula III. The reactions can be carried out using the methods described hereinabove for the preparation of compounds of Formula I by the reaction of compounds of Formula II with compounds of Formula III.

Compounds of Formula I can additionally be prepared by the reaction of a 4-iodo-3-substituted-2-(substituted-phenyl)(alkylsulfonyl)benzene compound (a substituted 2-substituted-3-iodo-6-alkylsulfonylbiphenyl compound) of Formula X:

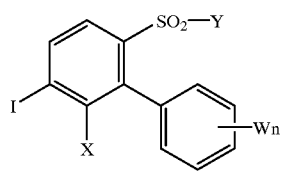

wherein X, Y, W, and n are as defined for compounds of Formula I with a 1-hydrocarbyl-5-hydroxypyrazole compound of Formula III and carbon monoxide. The reaction is generally carried out in the presence of a tertiary amine compound, such as triethylamine, and of a palladium(0) catalyst, such as tetrakis(triphenylphosphine)-palladium(0) or a mixture of palladium(II) acetate and tri-o-tolylphosphine. The analogous 4-bromo-3-substituted-2-(substituted-phenyl)(alkylsulfonyl)benzene compounds undergo this reaction and can often be used as well. Considerable amounts of by-product are typically obtained in this procedure when X represents bromo, but the desired compounds of Formula I are obtained and can be recovered. Typically, the compound of Formula X, the hydroxypyrazole compound of Formula III, the tertiary amine compound, the catalyst, and a solvent, such as acetonitrile, are combined and carbon monoxide gas is added to the mixture under pressure. The mixture is then heated under pressure at about 100° C. to about 120° C. for up to 30 hours. The reaction conditions employed, which are exemplified herein, are essentially the same as those disclosed in U.S. Patent RE34,408 for the preparation of related compounds. Similarly, compounds of Formula I can be prepared from a 4-iodo-3-substituted-2-(substituted-phenyl)(alkylthio)benzene compound (a 2-substituted-3-iodo-6-alkylthiobiphenyl compound) of Formula XI:

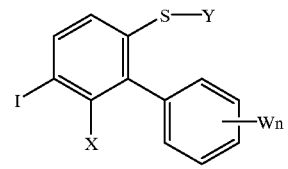

wherein X, Y, W, and n are as defined for compounds of Formula I or a 4-bromo analog thereof. The compound of Formula XI, a compound of Formula II, and carbon monoxide are heated in the presence of a trialkylamine compound, such as triethylamine, and a palladium(0) catalyst, such as tetrakis(triphenylphosphine)palladium(0) or palladium(II) acetate and tri-o-tolylphosphine and the (4-alkylthiobenzoyl)pyrazole compound obtained as a product is oxidized with meta-chloroperbenzoic acid or another suitable oxidizing agent to convert the alkylthio group (S—Y) to an alkylsulfonyl (SO$_2$—Y) group.

Compounds of Formula XI can be prepared from the corresponding 2-substituted-3-(substituted-phenyl)-4-alkylthioaniline compounds of Formula XII:

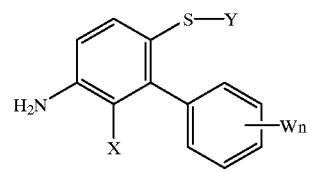

wherein X, Y, W, and n are as defined for compounds of Formula I by diazotization with nitrous acid and treatment of the diazonium salt obtained with potassium iodide under reaction conditions well-known in the art and exemplified herein. The corresponding bromo compounds can be prepared analogously. Compounds of Formula XI can also be made by conversion of the corresponding 4-thiocyano compounds (compounds of Formula XI wherein Y represents CN) to 4-alkylthio compounds by treatment with sodium sulfide and an alkyl iodide under conditions well established in the art for this type of reaction.

Compounds of Formula X can be prepared from compounds of Formula XI by oxidation with meta-chloroperbenzoic acid or another suitable oxidizing agent using reaction conditions well known in the art and exemplified herein.

2-Substituted-3-(substituted-phenyl)-4-alkylthioaniline compounds of Formula XII can be prepared by the reaction of the corresponding 4-thiocyano compounds with sodium sulfide and an alkyl iodide under conditions well established in the art for such reactions and exemplified herein. The 4-thiocyano compounds required for this method can, in turn, be prepared by thiocyanation of corresponding 2-substituted-3-(substituted-phenyl)aniline compounds of Formula XIII:

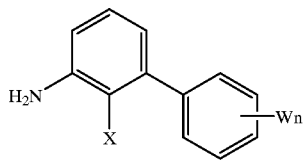

wherein X, W, and n are as defined for compounds of Formula I under reaction conditions exemplified herein and well established in the art for related reactions. Aniline compounds of Formula XIII can be prepared by reduction of the corresponding nitro compounds, which, in turn, can be prepared by phenylation of 2-substituted-3-iodonitrobenzene compounds with optionally substituted phenylboronic acid compounds of Formula V. Reaction conditions for these methods are exemplified herein and are essentially the same as those described hereinabove for related Suzuki-Miyaura type conversions.

Compounds of Formula I wherein Z represents hydrogen can be converted into corresponding compounds of Formula I wherein Z represents optionally substituted benzyl by treatment with an optionally substituted benzyl chloride or bromide using reaction conditions exemplified herein and well known in the art and to promote similar etherification reactions. For example, approximately equimolar amounts of the reactants can be combined in an alcohol or a dipolar, aprotic solvent, a non-reactive base, such as a tertiary amine or an alkali metal carbonate, added, and the mixture heated. Salts of compounds of Formula I wherein Z represents hydrogen can be prepared by treatment with an equimolar amount of an appropriate metal hydroxide, amine, or aminium hydroxide compound. Esters of compounds of Formula I wherein Z represents hydrogen can be made by treatment with equimolar amounts of an appropriate acid chloride compound and a tertiary amine compound, typically in an inert organic solvent. Reaction conditions known in the art for similar esterification reactions and exemplified herein can be used. In each case the compounds prepared can be recovered by standard techniques.

The compounds of Formula I have been found to be useful preemergence and postemergence herbicides. They can be employed at non-selective (higher) rates of application to control a broad spectrum of the vegetation in an area or, in most cases, at selective (lower) rates of application for the selective control of undesirable vegetation in grass crops, such as corn, wheat, barley, rice, and turf as well as in broadleaf crops, such as soybeans and cotton. It is usually preferred to employ the compounds postemergence. It is further usually preferred to use the compounds to control a broad spectrum of weeds, including grassy weeds, such as barnyardgrass and giant foxtail, in crops, such as rice, wheat, barley, and turf. While each of the benzoylpyrazole compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient which kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I post-emergence to relatively immature undesirable vegetation to achieve the maximum control.

Application rates of about 1 to about 500 g/Ha are generally employed in postemergence operations; for preemergence applications, rates of about 10 to about 1000 g/Ha are generally employed. The higher rates designated generally give non-selective control of a broad variety of undesirable vegetation. The lower rates typically give selective control and, by judicious election, can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam, and N-2,6-difluorophenyl-5-methoxy-8-fluoro[1,2,4]triazolo-[1,5-c]pyrimidine-2-sulfonamide, sulfonylureas such as chlorimuron, nicosulfuron and metsulfuron, imidazolidones such as imazaquin, imazethapyr and imazamox, phenoxyalkanoic acids such as 2,4-D and MCAA, pyridinyloxyacetic acids such as triclopyr and fluroxypyr, carboxylic acids such as clopyralid and dicamba, dinitroanilines such as trifluralin and pendimethalin, and other common herbicides including acifluorfen, bentazon, clomazone, fumiclorac, fluometuron, fomesafen, lactofen, linuron, isoproturon, and metribuzin. They can, further, be used in conjunction with glyphosate and glufosinate. It is generally preferred to use the compounds of the invention in combination with herbicides that are selective for the crop being treated and which complement the spectrum of weeds controlled by these compounds at the application rate employed. It is further generally preferred to apply the compounds of the invention and complementary other herbicides at the same time, either as a combination formulation or as a tank mix.

The compounds of the present invention can generally be employed in combination with known herbicide safeners, such as cloquintocet, furilazole, dichlormid, benoxacor, flurazole, fenchlorazole-ethyl, mefenpyr, and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are quinone biosynthesis inhibitors in sensitive plants can be treated.

Many glyphosate and glufosinate tolerant crops can be treated as well.

While it is possible to utilize the benzoylpyrazole compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic, or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea, and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

EXAMPLES

The following Examples are presented to illustrate the various aspects of this invention and should not be construed as limitations to the claims.

1. Preparation of 3-Iodo-2-methyl-4-methylsulfonylbenzoic Acid

A) 3-Amino-2-methyl-4-methylsulfonylbenzoic Acid

A mixture of 79.0 g (grams)(320 mmol (millimole)) of 3-chloro-2-methyl-4-methylsulfonylbenzoic acid, 1.0 g (12.6 mmol) of cupric oxide, and 500 mL (milliliter) of concentrated aqueous ammonia was heated at 180° C. for 17 hours in a stirred Parr reactor. The resulting dark mixture was concentrated by evaporation under reduced pressure. The residue was acidified with 2N aqueous hydrochloric acid and the resulting mixture was extracted with ethyl acetate. The extract was filtered and concentrated by evaporation under reduced pressure. The solid residue was mixed with hexane, recovered by filtration, and dried to obtain 50.0 g (68 percent of theory) of the title acid compound as a light tan powder melting at 197–198° C.

$^1$H NMR($d_6$-DMSO) (dimethylsulfoxide) : ppm 13.25(s, 1H), 7.50(d, 1H, J=8 Hz), 6.92(d, 1H, J=8 Hz), 5.97(s, 2H), 3.12(s, 3H), 2.22(s, 3H).

B) Ethyl 3-Amino-2-methyl-4-methylsulfonylbenzoate

3-Amino-2-methyl-4-methylsulfonylbenzoic acid (50.0 g, 0.22 mol) was combined with 500 mL of ethanol and 25 mL of concentrated sulfuric acid and the mixture was heated at reflux overnight. The resulting mixture was partially concentrated by evaporation under reduced pressure and the residue was poured onto ice. Water was added and the resulting mixture was extracted with ethyl acetate. The extract was washed with dilute aqueous sodium hydroxide, filtered, and concentrated by evaporation under reduced pressure to obtain 51.3 g (86 percent of theory) of the ethyl ester as a tan solid melting at 108–109° C.

$^1$H NMR($d_6$-DMSO): ppm 7.52(d, 1H, J=8 Hz), 6.92(d, 1H, J=8 Hz), 6.02(s, 2H), 4.28(q, 2H, J=7 Hz), 3.14(s, 3H), 2.20(s, 3H), 1.28(t, 3H, J=7 Hz).

C) Ethyl 3-Iodo-2-methyl-4-methylsulfonylbenzoate

A first solution of 54.0 g (0.21 mol) of ethyl 3-amino-2-methyl-4-methylsulfonylbenzoate in 250 mL of concentrated aqueous hydrochloric acid was prepared and cooled to 0° C. with a dry ice/2-propanol bath. A second solution of 21.7 g (0.315 mol) of sodium nitrite in 40 mL of water was prepared and was added to the first solution dropwise with stirring and cooling (by adding dry ice to the bath) to keep the temperature below 0° C. The resulting yellow orange solution containing some solids was added slowly with stirring to a solution of 52.3 g (0.315 mol) of potassium iodide in 500 mL of water. Nitrogen gas was evolved and the mixture turned dark brown. Dichloromethane was added to facilitate stirring and the mixture was stirred for 30 min. Sodium sulfite was then added to remove some of the color and the resulting mixture was extracted three times with dichloromethane. The combined extracts were washed with water, dried over magnesium sulfate, and concentrated by evaporation under reduced pressure. The yellow solid residue was recrystallized from ethanol to obtain 68.5 g (89 percent of theory) of the title compound as pale yellow crystals. The compound melts at 104–1050° C.

$^1$H NMR(CDCl$_3$): ppm 8.13 (d, 1H, J=8 Hz), 7.78 (d, 1H, J=8 Hz), 4.41(q, 2H, J=7 Hz), 3.32(s, 3H), 2.74(s, 3H), 1.38(t, 3H, J=7 Hz)

Ethyl 2-chloro-3-iodo-4-methylsulfonylbenzoate was prepared similarly.

C) 3-Iodo-2-methyl-4-methylsulfonylbenzoic Acid

A solution of 18.2 g (276 mmol) of 85 percent potassium hydroxide in 100 mL of water was added to a mixture of 67.8 g (184 nunol) of ethyl 3-iodo-2-methyl-4-methylsulfonylbenzoate in 300 mL of ethanol with stirring. After about 1 hour, all of the solids had dissolved and after 2 hours the mixture was concentrated by evaporation under reduced pressure. The residue obtained was diluted with water and the solution obtained was extracted with ether and then diluted with ethyl acetate. Aqueous hydrochloric acid (3N) was then added until the mixture was acidic. The organic phase was separated and the aqueous phase was twice extracted with ethyl acetate. The organic phase and extracts were combined and washed with saturated aqueous sodium chloride solution, dried over magnesium sulfate, and concentrated by evaporation under reduced pressure. The 62.1 g (99 percent of theory) of colorless solid residue was the title compound. The purified compound melts at 193° C.

$^1$H NMR(d$_6$-DMSO): ppm 13.80 (s, 1H), 7.98(d, 1H, J=8 Hz), 7.80(d, 1H, J=8 Hz), 3.40(s, 3H), 2.62(s, 3H).

2. Preparation of 1-(1,1-Dimethylethyl)-5-hydroxy-4-(3-iodo-2-methyl-4-methylsulfonylbenzoyl) pyrazole A solution of 8.4 g (40 mmol) of 1,3-dicyclohexylcarbodiimide in 40 mL of acetonitrile was added to a mixture of 13.6 g (40 mmol) of 3-iodo-2-methyl-4-methylsulfonylbenzoic acid and 5.6 g (40 mmol) of 1-(1,1-dimethylethyl)-5-hydroxypyrazole in 80 mL of acetonitrile with stirring. The mixture was allowed to stir for 1 hour and was then filtered, washing the filter cake with a little acetonitrile. Triethylamine (16.8 mL, 120 mmol) and acetone cyanohydrin (1 mL, 10 mmol) were added with stirring to the filtrate. After about 1.5 hour, dichloromethane was added and the resulting mixture was washed with a mixture of 2N aqueous hydrochloric acid and saturated aqueous sodium chloride. It was then concentrated by evaporation under reduced pressure. The residue obtained was dissolved in dichloromethane and the resulting solution was extracted with dilute aqueous sodium hydroxide. The aqueous extract was acidified with concentrated aqueous hydrochloric acid and the resulting mixture was extracted with dichloromethane. Fifty mL of triethylamine was added to the dichloromethane extract and the resulting solution was washed with saturated aqueous sodium chloride solution and then several times with 2N aqueous hydrochloric acid. It was then concentrated by evaporation under reduced pressure. The residue was triturated with hexane to obtain 16.8 g (72.7 percent of theory of the title compound as a light yellow powder melting at 171–172° C.

Elemental Analysis C$_{16}$H$_{19}$N$_2$IO$_4$S

Calc.: % C, 41.6; % H, 4.14; % N, 6.06

Found: %C, 41.7; % H, 4.16; % N, 6.00.

3. Preparation of 1-Ethyl-5-hydroxy-4-(3-iodo-2-methyl-4-methylsulfonylbenzoyl) pyrazole Thionyl chloride (20 mL) was added to a mixture of 62.1 g (182 mmol) of 3-iodo-2-methyl-4-methylsulfonylbenzoic acid and 300 mL of 1,2-dichloroethane and the mixture was heated to reflux with stirring for 3 hours, absorbing the hydrogen chloride gas that evolved in an aqueous sodium hydroxide trap. The resulting solution was concentrated by evaporation under reduced pressure, diluted with 200 mL of toluene and reconcentrated by evaporation under reduced pressure. The resulting residue was dissolved in 100 mL of dichloromethane to obtain a first solution. A second solution was prepared by dissolving 22.3 g (270 mmol) of triethylamine and 24.7 g (270 mmol) of 1-ethyl-5-hydroxypyrazole in 200 mL of dichloromethane. This solution was cooled in an ice bath and the first solution was added to it dropwise with stirring and cooling. The resulting mixture was allowed to warm to ambient temperature and was then washed with cold 0.5N aqueous hydrochloric acid and then cold 5 percent aqueous potassium carbonate. It was then dried over magnesium sulfate and concentrated by evaporation under reduced pressure to obtain 84.2 g of a nearly colorless solid. This solid was slurried in 400 mL of dry acetonitrile and 1 mL (11 mmol) of acetone cyanohydrin and 37.7 g (270 mmol) of solid potassium carbonate were added. The mixture was allowed to stir overnight and was then concentrated by evaporation under reduced pressure. The residue was dissolved in water and the solution was extracted with ether and then acidified with 3N aqueous hydrochloric acid. The resulting mixture was extracted three times with dichloromethane and the combined extracts were dried over magnesium sulfate and concentrated by evaporation under reduced pressure. The gummy residue was crystallized by adding ethanol, heating to reflux, and allowing the solution to cool to obtain 63.3 g (68 percent of theory) of the title compound as yellow crystals. The compound melts at 149–150° C.

Elemental Analysis C$_{14}$H$_{15}$N$_2$IO$_4$S (typical sample)

Calc.: % C, 38.7; % H, 3.48; % N, 6.45; % S, 7.38

Found: % C, 39.5; % H, 3.54; % N, 6.44; % S, 7.49.

4. Preparation of 2-Methyl-4-methylsulfonyl-3-(4-methylthiophenyl)benzoic Acid

A mixture of 5.8 g (17 mmol) of 3-iodo-2-methyl-4-methylsulfonylbenzoic acid, 4.0 g (23.8 mmol) of 4-methylthiophenylboronic acid, 11.7 g (85 mmol) of potassium carbonate, 50 mL of acetonitrile, and 12 mL of water was prepared and purged with nitrogen gas with stirring. The catalyst system, 190 mg (0.85 mmol) of palladium II acetate and 775 g (2.25 mmol) of tri-o-tolylphosphine, was added and the mixture was heated to reflux with stirring for several hours. The mixture was then cooled, basified with dilute aqueous sodium hydroxide solution, extracted with ether, and then acidified with concentrated aqueous hydrochloric acid. The resulting mixture was extracted with ether and the extract was concentrated by evaporation under reduced pressure. The residue was diluted with ethyl acetate and again concentrated by evaporation under reduced pressure. The residue was chromatographed on a preparative C-18 high pressure liquid chromatography (HPLC) column eluting with a 60:40:0.05 mixture of acetonitrile, water, and acetic acid. The product fractions were combined and extracted with ether. The ethereal extracts were concentrated by evaporation under reduced pressure and the residue obtained was diluted with ethyl acetate and again concentrated by evaporation under reduced pressure. The residue obtained was mixed with hexane and the insoluble solids were recovered by filtration and dried to obtain 2.2 g (39 percent of theory) of the title compound as a tan powder melting at 178–179° C.

$^1$H NMR(CDCl$_3$): ppm 8.20(d, 1H, J=8 Hz), 8.08(d, 1H, J=8 Hz), 7.35(d, 2H, J=8 Hz), 7.20(d, 2H, J=8 Hz), 2.65(s, 3H), 2.55(s, 3H), 2.27(s, 3H).

2-Methyl-4-methylsulfonyl-3-(4-methoxyphenyl)-benzoic acid, a white solid, was prepared analogously.

5. Preparation of 2-Methyl-4-methylsulfonyl-3-(4-methylsulfonylphenyl)benzoic Acid A mixture of 2.2 g (6.5 mmol) of 2-methyl-4-methylsulfonyl-3-(4-methylthiophenyl)benzoic acid, 2.2 mL (19.6 mmol) of 30 percent hydrogen peroxide, and 25 mL of acetic acid was heated to 80° C. with stirring for 1 hour and was then allowed to stand overnight. The mixture was diluted with water, treated with sodium bisulfite, and then extracted with a mixture of ether and ethyl acetate. The extract was concentrated by evaporation under reduced pressure and the residue was diluted with dichloromethane. The resulting mixture was filtered and the solids that were collected were washed with ethyl acetate. The filtrate was found to contain only about 0.5 g of impure product and was discarded. The solids were dissolved (a slow process) in a mixture of ethyl acetate and water and the organic phase was separated and concentrated by evaporation under reduced pressure. The resulting solid residue was diluted with hexane and the insoluble solids were recovered by filtration and dried to obtain 2.1 g (88 percent of theory) of the title compound as a white powder melting at 214–215° C.

$^1$H NMR(d$_6$-DMSO): ppm 8.02(m, 3H), 7.93(d, 1H, J=8 Hz), 7.57(d, 2H, J=8 Hz), 3.32(s, 3H), 2.90(s, 3H), 2.02(s, 3H).

6. Preparation of 4-(Trifluoromethyloxy) phenylboronic Acid Anhydride Trimer A dilute solution of n-butyllithium was prepared by diluting 8.0 mL of commercial 2.5M solution with 20 mL of dry tetrahydrofuran (THF) and the solution obtained was cooled to −90° C. with liquid nitrogen. A solution of 5.0 g of 4-(trifluoromethoxy)bromobenzene in 5 mL of dry THF was added dropwise with stirring and cooling to keep the temperature at about −90° C. After the addition, the mixture was allowed to stir for 30 min and then 6.9 mL of tri(1-methylethyl) borate in 5 mL of dry THF was added dropwise with stirring and cooling to maintain the temperature at about −90° C. The stirred mixture was allowed to warm to −70° C. and was held there for 30 min. It was then allowed to warm to ambient temperature over a 1-hour period. Twenty mL of 2N aqueous hydrochloric acid was added with stirring and the resulting mixture was extracted with 40 mL of ether. The ether extract was washed with water and then extracted with 20 mL of 2N aqueous sodium hydroxide solution. The aqueous extract was acidified with concentrated aqueous hydrochloric acid and extracted with ether. The ether extract was washed with saturated aqueous sodium chloride solution, dried over sodium sulfate, and concentrated by evaporation under reduced pressure. The residue was removed from the flask with the aid of cold pentane and recovered by filtration to obtain 3.1 g of the title compound as a white solid melting at 115–119° C. The solid was shown to be the anhydride trimer by mass spectrometry.

Elemental Analysis $C_{21}H_{12}F_9B_3O_6$

Calc.: % C, 44.7; % H, 2.14

Found: % C, 44.2; % H, 2.23.

The following substituted phenylboronic acid compounds and/or the anhydride trimers thereof were among those prepared analogously from the corresponding bromobenzene compounds:

1) 3-(trifluoromethyloxy)phenylboronic acid, a white solid melting at 74–77° C.;
2) 4-chloro-3-methylphenylboronic acid, a white solid melting at 249–255° C.;
3) 3-chloro-4-methylphenylboronic acid, a white solid melting at 180–190° C.;
4) 4-(methoxymethoxy)phenylboronic acid, a pale pink crystalline solid melting at 130–133° C.;
5) 3-(methoxymethoxy)phenylboronic acid, a waxy solid;
6) 3,4-(ethylenedioxy)phenylboronic acid, a white powder melting at 238–241° C.;
6) 3,4-(methylenedioxy)phenylboronic acid, a brown powder melting at 237–240° C.;
7) 3,4-dichlorophenylboronic acid;
8) 3,4-dimethoxyphenylboronic acid;
9) 4-(2-methoxyethoxy)phenylboronic acid;
10) 3-(2-methoxyethoxy)phenylboronic acid;
11) 4-methoxy-3-methylphenylboronic acid;
12) 4-(2-propenyloxy)phenylboronic acid;
13) 3-(2-propenyloxy)phenylboronic acid;
14) 4-fluorophenylboronic. acid;
15) 3-fluorophenylboronic acid;
16) 4-ethenylphenylboronic acid;
17) 3,5-dimethylphenylboronic acid, a white solid;
18) 3-chloro-5-methylphenylboronic acid;
19) 2-chlorophenylboronic acid, a white solid;
20) 3-fluoro-4-methoxyphenylboronic acid, a light yellow solid;
21) 3-chloro-4-methoxyphenylboronic acid, a light yellow solid melting at 210° C.;
22) 4-ethoxyphenylboronic acid, a fluffy white solid melting at 165° C.;
23) 3-(1-methylethoxy)phenylboronic acid, a fluffy white solid melting at 81° C.;
24) 4-(1-methylethoxy)phenylboronic acid, a fluffy white solid melting at 75° C.;
26) 3-(1-methylethyl)phenylboronic acid, a white solid melting at 68–75° C.;
27) 4-(1-methylethyl)phenylboronic acid, a white solid melting at 90–118° C.;
28) 4-ethylphenylboronic acid; a white solid melting at 90–130° C.;
29) 3-ethylphenylboronic acid; a white solid melting at 75–88° C.;
30) 4-chloro-3-methoxyphenylboronic acid, a light tan solid melting at 107–150° C.;
31) 2-methylphenylboronic acid;
32) 2-methoxyphenylboronic acid;

7. Preparation of 2-Chloro-4-methylsulfonyl-3-phenylbenzoic Acid

A) 2-Chloro-6-methylthioaniline

A mixture of 36.0 g (196 mmol) of 2-amino-4-chlorobenzothiazole, 108 g (2.8 mmol) of sodium hydroxide, and 480 mL of water was heated at reflux with stirring for 4.5 hours. The resulting mixture was cooled and diluted with 180 mL of water. Six drops of tetrabutylammonium hydroxide were added and then 22.5 mL (235 mmol) of dimethyl sulfate dissolved in 50 mL of toluene was added dropwise over a 20-min period with stirring. The mixture was stirred another 30 min at ambient temperature. Ether was added and the phases were separated. The aqueous phase was extracted with ether. The combined organic phase and extract were treated with dimethylamine to destroy excess dimethyl sulfate, washed with water, dried, and concentrated by evaporation under reduced pressure. The residual liquid was distilled at 1 mm (millimeter) Hg (130 Pascals) pressure and the 18 g (53 percent of theory) colorless liquid fraction boiling at 100° C. was collected and shown to be the title compound.

$^1$H NMR(CDCl$_3$): ppm 7.26(d, 1H) , 7.19(d, 1H), 6.64 (dd, 1H), 4,65(brs, 2H), 2.37(s, 3H).

B) 3-Chloro-2-iodo(methylthio)benzene

2-Chloro-6-methylthioaniline (15.0 g, 87 mmol) was dissolved in 200 mL of concentrated hydrochloric acid and the resulting solution was cooled to 0° C. to −10° C. with a dry ice/methanol bath. A solution of 8.9 g (130 mmol) of sodium nitrite in 30 mL of water was added dropwise with stirring and cooling to maintain the temperature below 0° C. The solution was then stirred for 20 min at 0° C. A mixture of 22 g (130 mmol) of potassium iodide dissolved in 300 mL of water and 200 mL of dichloromethane was prepared and the solution prepared above was added to it in portions with stirring. The mixture was allowed to react for 20 min at ambient temperature. A small amount of aqueous sodium bisulfite solution was added and then the phases were separated. The organic phase was washed twice with 2N aqueous hydrochloric acid and once with saturated aqueous sodium chloride solution, dried over sodium sulfate, and concentrated by evaporation under reduced pressure. The residue was crystallized with heptane and chromatographed on silica eluting with an 85:15 mixture of hexane and dichloromethane to obtain 13.5 g of the title compound as a crystalline, low melting yellow solid.

$^1$H NMR(CDCl$_3$): ppm 7.25(m, 2H), 6.92(m, 1H), 2.46(s, 3H).

C) 3-Chloro-2-phenyl(methylthio)benzene (2-Chloro-6-methylthiobiphenyl)

A mixture of 6.0 g (21 mmol) of 3-chloro-2-iodo (methylthio)benzene, 5.1 g (42 mmol) of phenylboronic acid, 14 g (100 mmol) of potassium carbonate, 80 mL of 1,2-dimethoxyethane, and 75 mL of water was prepared and deaerated with a stream of nitrogen. Tetrakis (triphenylphosphine)palladium(0) (730 mg, 0.63 mmol) was added and the mixture was heated at about 100° C. under nitrogen with stirring for about 20 hours. Water and ether were added and the aqueous phase was extracted with more ether. The ether phase and extract were combined, washed with saturated aqueous sodium chloride solution, dried over sodium sulfate, and concentrated by evaporation under reduced pressure and then in a Kugelrohr apparatus at 80° C. under 0.5 mm Hg (67 Pascals) pressure. The liquid residue was chromatographed on silica eluting with an 85:15 mixture of hexane and dichloromethane to obtain 4.3 g (87 percent of theory) of the title compound as a colorless liquid.

$^1$H NMR(CDCl$_3$): ppm 7.45(m, 3H), 7.25(m, 4H), 7.11 (m, 1H), 2.34(s, 3H).

D) 3-Chloro-4-bromo-2-phenyl(methylthio)benzene (2-Chloro-3-bromo-6-methylthiobiphenyl)

A solution of 3.3 g (20 mmol) of bromine dissolved in 10 mL of 1,2-dichloroethane was added dropwise with stirring to a solution of 4.0 g (17 mmol) of 3-chloro-2-phenyl (methylthio)benzene in 50 mL of 1,2-dichloroethane containing 3.1 g (19 mmol) of ferric chloride. The resulting mixture was allowed to react for another 1.5 hour and then another about 1 g of bromine was added. After 15 min, aqueous sodium bisulfite was added and the mixture was allowed to stand overnight. The organic phase was recovered, washed with water and with saturated aqueous sodium chloride solution, dried over sodium sulfate, and concentrated by evaporation under reduced pressure. The residue was chromatographed on silica eluting with a 5:1 mixture of hexane and dichloromethane to obtain 2.7 g (51 percent of theory) of the title compound as a colorless liquid.

$^1$H NMR(CDCl$_3$): ppm 7.60(d, 1H, J=8.6 Hz), 7.47(m, 3H), 7.22(m, 2H), 6.98(d, 1H, J=8.6 Hz), 2.32(s, 3H).

E) 3-Chloro-4-bromo-2-phenyl(methylsulfonyl) benzene (2-Chloro-3-bromo-6-methylsulfonylbiphenyl)

A solution of 2.5 g (8.0 mmol) of 3-chloro-4-bromo-2-phenyl(methylthio)benzene in 75 mL of dichloromethane was cooled with an ice bath and 5.7 g of meta-chloroperbenzoic acid was added in small portions with cooling and stirring. The mixture was allowed to warm to ambient temperature and stir overnight and was then heated to reflux for a short time. An aqueous solution of sodium bisulfite was added and the mixture was made basic with sodium carbonate. The organic phase was separated, washed with dilute aqueous sodium bicarbonate solution, water, and saturated aqueous sodium chloride solution, dried over sodium sulfate, and concentrated by evaporation under reduced pressure. The 3.0 g of residue was the title compound as a low melting white solid.

$^1$H NMR(CDCl$_3$): ppm 8.04(d, 1H) , 7.88(d, 1H), 7.50(m, 3H), 7.32(m, 2H), 2.62(s, 3H).

F) Methyl 2-Chloro-4-methylsulfonyl-3-phenyl-benzoate

A mixture of 2.6 g (7.5 mmol) of 3-chloro-4-bromo-2-phenyl(methylsulfonyl)benzene, 2.1 mL (15 mmol) of triethylamine, 67 mg (0.3 mmol) of palladium(II) acetate, 0.26 g (0.6 mmol) of 1,4-bis(diphenylphosphino)-butane, and 120 mL of deaerated methanol were placed in a 200 mL Parr reactor. The mixture was purged with carbon monoxide and then pressured with carbon monoxide to 300 psi (pounds per square inch)(21,000 kilopascals) and heated to 100° C. with stirring for 20 hours. The mixture was allowed to cool and was concentrated by evaporation under reduced pressure. The residue was partitioned between water and a mixture of dichloromethane and ether. The organic phase was washed with dilute aqueous hydrochloric acid and then saturated aqueous sodium chloride solution, dried over sodium sulfate, and concentrated by evaporation under reduced pressure. The residue was 2.5 g of the title compound as a colorless, glassy solid.

$^1$H NMR (CDCl$_3$): ppm 8.23 (d, 1H), 7.83(d, 1H), 7.51 (m, 3H), 7.33(m, 2H), 3.98(s, 3H), 2.62(s, 3H).

G) 2-Chloro-4-methylsulfonyl-3-phenylbenzoic Acid

Methyl 2-chloro-4-methylsulfonyl-3-phenyl-benzoate was hydrolyzed with sodium hydroxide in aqueous methanol solution and recovered using standard methodology to obtain the title compound, a white solid, which was used as an intermediate without further analysis.

2-Chloro-4-methylsulfonyl-3-(4-chlorophenyl)-benzoic acid, a white solid;

$^1$H NMR(d$_6$-DMSO): ppm 8.15(d, 1H, J=8.3 Hz), 7.97(d, 1H, J=8.3 Hz), 7.56(d, 2H, J=8.4 Hz), 7.38(d, 2H, J=8.4 Hz), 3.94(s, 3H);

and 2-chloro-4-methylsulfonyl-3-(4-methoxyphenyl) benzoic acid, a white solid;

$^1$H NMR(d$_6$-DMSO): ppm 8.13(d, 1H, J=8 Hz), 7.91(d, 1H, J=8 Hz), 7.26(d, 2H, J=8 Hz), 7.06(d, 2H, J=8 Hz), 3.84(s, 3H), 2.83(s, 3H).

were among the 3-phenylbenzoic acid compounds prepared analogously.

8. Preparation of 4-Iodo-3-methyl-2-(2-methylphenyl) (methylsulfonyl)benzene (3-Iodo-2,2'-dimethyl-6-methylsulfonylbiphenyl)

A) 2-Methyl-3-(2-methylphenyl)nitrobenzene (2,2'-Dimethyl-3-nitrobiphenyl)

A mixture of 81 mg (0.36 mmol) of palladium(II) acetate and 330 mg (1.1 mmol) of tri-o-tolylphosphine in 100 mL of dry 1,2-dimethoxyethane was stirred for 15 min and then 3.2 g (12 mmol) of 3-iodo-6-nitrotoluene was added with stirring. After 15 min, 2.2 g (16 mmol) of 2-methylphenylboronic acid in 15 mL of ethanol and 8.3 g (6.0 mmol) of potassium carbonate in 15 mL of water were added and the mixture was heated to 85° C. with stirring for 2 hours. The mixture was then allowed to cool and was diluted with water. The resulting mixture was extracted with ether and the ethereal extract was filtered, washed with saturated aqueous sodium chloride solution, dried over sodium sulfate, and concentrated by evaporation under reduced pressure. The about 5 g of residue, which was the title compound in impure form, was used without purification.

B) 2-Methyl-3-(2-methylphenyl)aniline (3-amino-2,2'-dimethylbiphenyl)

The about 5 g of 2-methyl-3-(2-methylphenyl)-nitrobenzene obtained in A) was dissolved in 150 mL of deaerated ethanol and placed in a Parr shaker flask. About 1 g of 5 percent palladium on carbon catalyst was added and the mixture was pressured with hydrogen. The hydrogenation was allowed to proceed overnight. The mixture was then filtered through diatomaceous earth and concentrated by evaporation under reduced pressure. The residue was dissolved in concentrated aqueous hydrogen chloride and the solution was washed with ether. The hydrochloride salt of the title compound precipitated from this mixture and was recovered by filtration and washed with ether. The recovered amine hydrochloride and filtrate were basified with aqueous sodium hydroxide and extracted with ether. The ether extract was washed with water and with saturated aqueous sodium chloride solution, dried over sodium sulfate, and concentrated under reduced pressure to obtain 1.9 g of the title compound.

$^1$H NMR(CDCl$_3$): ppm 7.4–7.0 (m, 5H), 7.73 (d, 2H), 7.62 (d, 1H), 3.64(brs, 2H), 2.07(s, 3H), 1.85(s, 3H).

C) 2-Methyl-3-(2-methylphenyl)-4-thiocyandaniline (3-amino-2,2'-dimethyl-6-thiocyanobiphenyl)

A solution of 1.5 g (7.6 mmol) of 2-methyl-3-(2-methylphenyl)aniline and 2.2 g of potassium thiocyanate in 25 mL of methanol was prepared and cooled to 0° C. A solution of 1.3 g (8.4 mmol) of bromine in 10 mL of dichloromethane was added to this dropwise with stirring and cooling to keep the temperature below 0° C. A precipitate began to form immediately. After the addition was complete, the mixture was allowed to warm to ambient temperature and was stirred for another hour. Two mL of saturated sodium sulfite was added and the mixture was stirred for about 5 min. It was then diluted with water and the resulting mixture was extracted with ether. The ether phase was washed with water and with saturated aqueous sodium chloride solution, dried over sodium sulfate, and concentrated by evaporation under reduced pressure. The 1.9 g (97 percent of theory) of thick oil residue was the title compound.

$^1$H NMR(CDCl$_3$): ppm 7.44 (d, 1H), 7.30 (m, 3H), 7.03 (d, 1H), 6.76(d, 1H), 3.91(brs, 2H), 2.02(s, 3H), 1.80(s, 3H).

D) 2-Methyl-3-(2-methylphenyl)-4-methylthioaniline (3-amino-2,2'-dimethyl-6-methylthiobiphenyl)

A solution of 2.0 g (7.9 mmol) of 2-methyl-3-(2-methylphenyl)-4-thiocyanoaniline in 15 mL of ethanol was added dropwise over a 20-min period with stirring to a solution of 2.2 g of sodium sulfide nonahydrate (9.1 mmol) in 5 mL of water. The mixture was stirred at ambient temperature for 2 hours and was then cooled with an ice/salt bath. A solution of 1.5 g (11 mmol) of methyl iodide in 5 mL of ethanol was added with stirring over a 10-min period. The mixture was diluted with water and the resulting mixture was extracted with ether. The ethereal extract was washed with water, dried over sodium sulfate, and concentrated by evaporation under reduced pressure. The 2.0 g of residue was the title compound of about 80 percent purity.

$^1$H NMR(CDCl$_3$): ppm 7.44(d, 1H), 7.30(m, 3H), 7.03(d, 1H), 6.76(d, 1H), 3.90(brs, 2H), 2.02(s, 3H), 1.80(s, 3H), 1.56(s, 3H).

E) 4-Iodo-3-methyl-2-(2-methylphenyl) (methylthio)-benzene (3-iodo-2,2'-dimethyl-6-methylthiobiphenyl)

A solution of 2.0 g (8.2 mmol) of 85 percent purity 2-methyl-3-(2-methylphenyl)-4-methylthioaniline in 3 mL of dichloromethane was combined with 60 mL of concentrated aqueous hydrochloric acid and the mixture was stirred for 1 hour. It was then cooled to 5° C. A solution of 850 mg (12 mmol) of sodium nitrite in 10 mL of water was added in portions with stirring and cooling. After 45 min, this mixture was poured with stirring into a mixture of a solution of 2.0 g (12 mmol) of potassium iodide in 100 mL of water and 75 mL of dichloromethane and the combination was stirred for 30 min. Five mL of saturated sodium sulfite solution was then added with stirring and after 20 min reaction time, the phases were separated. The organic phase was washed with water and with saturated aqueous sodium chloride solution, dried over sodium sulfate, and concentrated under reduced pressure. The 2.4 g (83 percent of theory) of oily residue obtained was the title compound in impure form.

F) 4-Iodo-3-methyl-2-(2-methylphenyl)(methylsulfonyl)benzene (3-Iodo-2 21-dimethyl-6-methylsulfonylbiphenyl)

Solid meta-chloroperbenzoic acid (4.9 g, 17 mmol) was added in small portions with stirring and cooling at 5–10° C. to a solution of 2.4 g (6.8 mmol) of 4-iodo-3-methyl-2-(2-methylphenyl)(methylthio)benzene in 50 mL of dichloromethane. The mixture was allowed to warm to ambient temperature and stir overnight. A few mL of aqueous sodium sulfite solution was added with stirring and, after a negative starch-iodide test was obtained, the phases were separated. The organic phase was washed twice with dilute sodium bicarbonate, twice with water, and once with saturated aqueous sodium chloride solution and was then dried over sodium sulfate and concentrated by evaporation under reduced pressure. The residue was the title compound.

The following 4-iodo-3-methyl-2-(substituted-phenyl)(methylsulfonyl)benzene compounds were among those prepared analogously:
1) 4-iodo-3-methyl-2-(2-methoxyphenyl)(methylsulfonyl)-benzene;
2) 4-iodo-3-methyl-2-(2-chlorophenyl)(methylsulfonyl)-benzene;
3) 4-iodo-3-methyl-2-(2-fluorophenyl)(methylsulfonyl)-benzene;
4) 4-iodo-3-methyl-2-(2-fluoro-4-methoxyphenyl)(methylsulfonyl)benzene;
5) 4-iodo-3-methyl-2-(2,4-dichlorophenyl)(methylsulfonyl)benzene; and
6) 4-iodo-3-methyl-2-(2-chloro-4-methoxyphenyl)(methylsulfonyl)benzene.

9. Preparation of 1-Ethyl-5-hydroxy-4-(2-methyl-4-methylsulfonyl-3-(2-methylphenyl)benzoyl)pyrazole (Cpd. 16)

A mixture of 800 mg (2.1 mmol) of 4-iodo-3-methyl-2-(2-methylphenyl)(methylsulfonyl)benzene, 700 mg (6.2 mmol) of 1-ethyl-5-hydroxypyrazole, 1.2 mL (8.4 mmol) of triethylamine, 24 mg (0.11 mmol) of palladium (II) acetate, 100 mg (0.33 mmol) of tri-o-tolylphosphine, and 20 mL of dry acetonitrile was placed in a 45 mL Parr pressure reactor. The reactor was purged with carbon monoxide and then pressured to 300 psi (21,000 kilo-Pascals) with carbon monoxide and heated to 110° C. for 19 hours. The reactor was cooled and the mixture was concentrated by evaporation under reduced pressure. The residue was chromatographed by preparative HPLC with a YMC Corporation ODS-AQ column to separate the major product. The eluent, an acetonitrile/water mixture containing phosphoric acid, was extracted with dichloromethane and the extract was washed with water, dried over sodium sulfate, and concentrated by evaporation under reduced pressure. The residue was dissolved in a minimum amount of dichloromethane and then ether and hexane were added. The precipitate that formed was collected by filtration and dried to obtain 200 mg of the title compound as a white solid melting at 179–180° C.

The following benzoylpyrazole compounds were among those prepared analogously:
1) 1-Ethyl-5-hydroxy-4-(2-methyl-4-methylsulfonyl-3-(2-methoxyphenyl)benzoyl.)pyrazole (Cpd. 17);
2) 1-Ethyl-5-hydroxy-4-(2-methyl-4-methylsulfonyl-3-(2-fluorophenyl)benzoyl)pyrazole (Cpd. 18);
3) 1-Ethyl-5-hydroxy-4-(2-methyl-4-methylsulfonyl-3-(2-chlorophenyl)benzoyl)pyrazole (Cpd. 19);
4) 1-Ethyl-5-hydroxy-4-(2-methyl-4-methylsulfonyl-3-(2-fluoro-4-methoxyphenyl)benzoyl)pyrazole (Cpd. 21); and
5) 1-Ethyl-5-hydroxy-4-(2-methyl-4-methylsulfonyl-3-(2-chloro-4-methoxy phenyl)benzoyl)pyrazole (Cpd. 23).

10. Preparation of 1-(1,1-dimethylethyl)-5-hydroxy-4-(2-chloro-4-methylsulfonyl-3-phenylbenzoyl)pyrazole (Cpd. 2)

2-Chloro-3-phenyl-4-methylsulfonylbenzoic acid (750 mg, 2.4 mmol), excess oxalyl chloride, and a few drops of N,N-dimethylformamide were dissolved in 1,2-dichloroethane and the mixture was allowed to react with stirring overnight. The mixture was then concentrated by evaporation under reduced pressure. The residue was taken up in about 10 mL of dichloromethane and the resulting solution was cooled with an ice bath. To this was added 410 mg (2.9 mmol) of 1-(1,1-dimethylethyl)-5-hydroxypyrazole and about 2 mL of triethylamine. After about 1 hour, the mixture was diluted with-water and with more dichloromethane and the phases were separated. The organic phase was washed with dilute aqueous sodium bicarbonate, dried over sodium sulfate, and concentrated by evaporation under reduced pressure. The residue was dissolved in 10 mL of anhydrous 1,2-dimethoxyethane and 1.3 g (9.6 mmol) of sodium carbonate and then about 8 drops of acetone cyanohydrin were added. The mixture was allowed to react overnight and was then diluted with water. The phases were separated and the aqueous phase was extracted with ether, acidified with aqueous hydrochloric acid, and then twice extracted with dichloromethane. The dichloromethane extracts were combined and washed with saturated aqueous sodium chloride solution, dried over sodium sulfate, and concentrated by evaporation under reduced pressure. The 900 mg of residue was placed in 15 mL of ethanol and the mixture was heated and then cooled. The precipitate that formed was collected by filtration, washed with ether, and dried in a reduced pressure oven for 1 hour at 80° C. to obtain 682 mg (66 percent of theory) of the title compound as a tan solid melting at 262.5–264° C.

The following benzoylpyrazole compounds were among those prepared in an analogous way:
1) 1-ethyl-5-hydroxy-4-(2-chloro-4-methylsulfonyl-3-phenylbenzoyl)pyrazole (Cpd. 1);
2) 1-(1,1-dimethylethyl)-5-hydroxy-4-(2-chloro-4-methylsulfonyl-3-(4-chlorophenyl)benzoyl)pyrazole (Cpd. 4);
3) 1-ethyl-5-hydroxy-4-(2-chloro-4-methylsulfonyl-3-(4-chlorophenyl)benzoyl)pyrazole (Cpd. 3);
4) 1-(1,1-dimethylethyl)-5-hydroxy-4-(2-chloro-4-methylsulfonyl-3-(4-methoxyphenyl)benzoyl)pyrazole (Cpd. 20);
5) 1-(1-methylethyl)-5-hydroxy-4-(2-methyl-4-methylsulfonyl-3-(4-methoxyphenyl)benzoyl)pyrazole (Cpd. 13);
6) 1-(1,1-dimethylethyl)-S-hydroxy-4-(2-methyl-4-methylsulfonyl-3-(4-methoxyphenyl)benzoyl)pyrazole (Cpd. 14);
7) 1-methyl-5-hydroxy-4-(2-methyl-4-methylsulfonyl-3-(4-methoxyphenyl)benzoyl)pyrazole (Cpd. 15); and
8) 1-(1-methylpropyl)-5-hydroxy-4-(2-methyl-4-methylsulfonyl-3-(4-methoxyphenyl)benzoyl)pyrazole (Cpd. 22).

11. Preparation of 1-(1,1-dimethylethyl)-5-hydroxy-4-(2-methyl-4-methylsulfonyl-3-(4-methylsulfonylphenyl)-benzoyl)pyrazole (Cpd. 67)

A solution of 560 mg (2.7 mmol) of 1,3-dicyclohexylcarbodiimide in 5 mL of acetonitrile was added with stirring to a mixture of 2-methyl-4-methylsulfonyl-3-(4-methylsulfonylphenyl)benzoic acid and 378 mg (2.7 mmol) of 1-(1,1-dimethylethyl)-5-hydroxypyrazole in 15 mL of acetonitrile. The mixture was allowed to react for 1 hour and was then filtered. The solids were washed with a little acetonitrile. Triethylamine (1.13 mL, 8.1 mmol) and 274 microliters (2.7 mmol) of acetone cyanohydrin were added with stirring to the combined filtrate and acetonitrile wash. After 3 hours, the mixture was diluted with dichloromethane and the resulting solution was washed with 2N aqueous hydrochloric acid, filtered, and concentrated by evaporation under reduced pressure. The residue was dissolved in the minimum amount of hot ethanol and the solution was then cooled. The precipitate that formed was collected by filtration and dried to obtain the title compound as a pale yellow powder melting at 187–188° C.

1-Ethyl-5-hydroxy-4-(2-methyl-4-methylsulfonyl-3-(4-methylsulfonylphenyl)benzoyl)pyrazole (Cpd. 66) was prepared analogously.

12. Preparation of 1-(1,1-dimethylethyl)-5-hydroxy-4-(2-methyl-4-methylsulfonyl-3-(4-ethoxyphenyl)benzoyl)-pyrazole (Cpd. 36)

A mixture of 1.0 g (2.2 mmol) of 1-(1,1-dimethylethyl)-5-hydroxy-4-(3-iodo-2-methyl-4-methylsulfonylbenzoyl)pyrazole, 0.541 g (3.3 mmol) of 4-ethoxyphenylboronic acid, 0.607 g (4.4 mmol) of potassium carbonate, 0.025 g (0.11 mmol) of palladium(II) acetate, 0.100 g (0.33 mmol) of tri-o-tolylphosphine, 25 mL of acetonitrile, and 3 mL of water was heated at reflux with stirring for 15 min. The resulting mixture was cooled and diluted with water. The mixture obtained was extracted with ether and acidified with concentrated aqueous hydrochloric acid. The yellow precipitate that formed was collected by filtration and recrystallized by dissolving in dichloromethane and then adding hexane to obtain 800 mg (80 percent of theory) of the title compound as a-white solid melting at 110° C.

The following benzoylpyrazole compounds were among those prepared in an analogous way:

1) 1-ethyl-5-hydroxy-4-(2-methyl-4-methylsulfonyl-3-(4-methoxyphenyl)benzoyl)pyrazole (Cpd. 10);
2) 1-(1,1-dimethylethyl)-5-hydroxy-4-(2-methyl-4-methylsulfonyl-3-(4-methoxyphenyl)benzoyl)pyrazole (Cpd. 14);
3) 1-ethyl-5-hydroxy-4-(2-methyl-4-methylsulfonyl-3-(4-(1-methylethoxyphenyl)benzoyl)pyrazole (Cpd. 35);
4) 1-(1,1-dimethylethyl)-5-hydroxy-4-(2-methyl-4-methylsulfonyl-3-(4-(1-methylethoxyphenyl)benzoyl)pyrazole (Cpd. 37);
5) 1-ethyl-5-hydroxy-4-(2-methyl-4-methylsulfonyl-3-(4-(2-propenyloxyphenyl)benzoyl)pyrazole (Cpd. 60);
6) 1-(1,1-dimethylethyl)-5-hydroxy-4-(2-methyl-4-methylsulfonyl-3-(4-(2-propenyloxyphenyl)benzoyl)pyrazole (Cpd. 38);
7) 1-ethyl-5-hydroxy-4-(2-methyl-4-methylsulfonyl-3-(4-(methoxymethoxyphenyl)benzoyl)pyrazole (Cpd. 26);
8) 1-(1,1-dimethylethyl)-5-hydroxy-4-(2-methyl-4-methylsulfonyl-3-(4-(methoxymethoxyphenyl)benzoyl)pyrazole (Cpd. 28);
9) 1-methyl-5-hydroxy-4-(2-methyl-4-methylsulfonyl-3-(4-methoxyphenyl)benzoyl)pyrazole (Cpd. 15);
10) 1-(1-methylethyl)-5-hydroxy-4-(2-methyl-4-methylsulfonyl-3-(4-methoxyphenyl)benzoyl)pyrazole (Cpd. 13);
11) 1-ethyl-5-hydroxy-4-(2-methyl-4-methylsulfonyl-3-(3,4-methylenedioxyphenyl)benzoyl)pyrazole (Cpd. 62);
12) 1-(1,1-dimethylethyl)-5-hydroxy-4-(2-methyl-4-methylsulfonyl- 3-(3,4-methylenedioxyphenyl)benzoyl)pyrazole (Cpd. 63);
13) 1-ethyl-5-hydroxy-4-(2-methyl-4-methylsulfonyl-3-(3-methoxyphenyl)benzoyl)pyrazole (Cpd. 29);
14) 1-ethyl-5-hydroxy-4-(2-methyl-4-methylsulfonyl-3-(4-trifluoromethoxyphenyl)benzoyl)pyrazole (Cpd. 40);
15) 1-ethyl-5-hydroxy-4-(2-methyl-4-methylsulfonyl-3-(4-ethylphenyl)benzoyl)pyrazole (Cpd. 44);
16) 1-ethyl-5-hydroxy-4-(2-methyl-4-methylsulfonyl-3-(3-chloro-4-methoxyphenyl)benzoyl)pyrazole (Cpd. 32);
17) 1-ethyl-5-hydroxy-4-(2-methyl-4-methylsulfonyl-3-(3,4-dimethoxyphenyl)benzoyl)pyrazole (Cpd. 55);
18) 1-(1,1-dimethylethyl)-5-hydroxy-4-(2-methyl-4-methylsulfonyl-3-(3,4-dimethoxyphenyl)benzoyl)pyrazole (Cpd. 58);
19) 1-ethyl-5-hydroxy-4-(2-methyl-4-methylsulfonyl-3-(4-fluorophenyl)benzoyl)pyrazole (Cpd. 48);
20) 1-ethyl-5-hydroxy-4-(2-methyl-4-methylsulfonyl-3-(3,5-dimethylphenyl)benzoyl)pyrazole (Cpd. 51);
21) 1-ethyl-5-hydroxy-4-(2-methyl-4-methylsulfonyl-3-phenylbenzoyl)pyrazole (Cpd. 5);
22) 1-ethyl-5-hydroxy-4-(2-methyl-4-methylsulfonyl-3-(4-methylphenyl)benzoyl)pyrazole (Cpd. 6);
23) 1-ethyl-5-hydroxy-4-(2-methyl-4-methylsulfonyl-3-(3-methylphenyl)benzoyl)pyrazole (Cpd. 8);
24) 1-ethyl-5-hydroxy-4-(2-methyl-4-methylsulfonyl-3-(4-(trifluoromethyl)phenyl)benzoyl)pyrazole (Cpd. 7);
25) 1-ethyl-5-hydroxy-4-(2-methyl-4-methylsulfonyl-3-(4-chlorophenyl)benzoyl)pyrazole (Cpd. 9); and
26) 1-ethyl-5-hydroxy-4-(2-methyl-4-methylsulfonyl-3-(3,5-dichlorophenyl)benzoyl)pyrazole (Cpd. 12).

13. Preparation of 1-(1,1-dimethylethyl)-5-acetyloxy-4-(2-methyl-4-methylsulfonyl-3-(4-methoxyphenyl)benzoyl)-pyrazole (Cpd. 73)

A solution of 0.25 mL of acetyl chloride in 3 mL of dry dichloromethane was added slowly under nitrogen at 0° C. with stirring to a solution of 1.5 g (3.4 mmol) of 1-(1,1-dimethylethyl)-5-hydroxy-4-(2-methyl-4-methylsulfonyl-3-(4-methoxyphenyl)benzoyl)pyrazole and 0.52 mL of triethylamine in about 20 mL of dry dichloromethane. The mixture was allowed to warm to ambient temperature and stir for 2 hours and was then diluted with dichloromethane. The resulting solution was extracted with saturated aqueous sodium bicarbonate solution and with water, dried over magnesium sulfate, filtered, and concentrated by evaporation under reduced pressure. The residual yellow oil was chromatographed on silica gel eluting with a 50:50 mixture of ethyl acetate and hexane. The product fractions were combined and concentrated by evaporation under reduced pressure to obtain 1.03 g (62 percent of theory) of the title compound as a white powder melting at 160–163° C.

14. Preparation of 1-(1,1-dimethylethyl)-5-benzyloxy-4-(2-methyl-4-methylsulfonyl-3-(4-methoxyphenyl)benzoyl)-pyrazole (Cpd. 72)

Benzyl chloride (1.1 mL) was added with stirring under nitrogen to a mixture of 2.0 g (4.5 mmol) of 1-(1,1-dimethylethyl)-5-hydroxy-4-(2-methyl-4-methylsulfonyl-3-(4-methoxyphenyl)benzoyl)pyrazole and 1.3 g of sodium carbonate in about 20 mL of dry N,N-dimethylformamide and the resulting mixture was allowed to stir overnight. Ethyl acetate was then added and the resulting mixture was washed with water several times, dried over magnesium sulfate, filtered, and concentrated by evaporation under reduced pressure. The residual orange oil was chromatographed on silica eluting with an 80:20 mixture and then a 60:40 mixture of hexane and ethyl acetate. The product fractions were combined and concentrated by evaporation under reduced pressure and dried to obtain 1.73 g (72 percent of theory) of the title compound as a yellow glass.

15. Evaluation of Postemergence Herbicidal Activity

Seeds of the desired test plant species were planted in Grace-Sierra MetroMix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photo-period which was maintained at about 23–29° C. during the day and 22–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 3.

TABLE 3

POSTMERGENCE HERBICIDAL ACTIVITY

| Cpd. No. | Rate, ppm | BWCHK | BWCKB | BWLMQ | BWPIG | BWVIO | BWWBK |
|---|---|---|---|---|---|---|---|
| 1 | 62.5 | 40 | 90 | 100 | 100 | 40 | 100 |
| 2 | 15.6 | 45 | 90 | 85 | 50 | 85 | 80 |
| 3 | 31.3 | 20 | 90 | 95 | 100 | 50 | 40 |
| 4 | 31.3 | 60 | 80 | 90 | 85 | 80 | 20 |
| 5 | 31.5 | 75 | 90 | 95 | 100 | 75 | 85 |
| 6 | 62.5 | 85 | 95 | 90 | 100 | 80 | 75 |
| 7 | 31.3 | 75 | 90 | 95 | 100 | 65 | 55 |
| 8 | 62.5 | 80 | 95 | 80 | 100 | 75 | 65 |
| 9 | 62.5 | 85 | 90 | 100 | 100 | 75 | 100 |
| 10 | 31.3 | 80 | 90 | 80 | 100 | 65 | 75 |
| 11 | 31.3 | 70 | 95 | 98 | 100 | 70 | 65 |
| 12 | 15.6 | 75 | 95 | 100 | 80 | 65 | 25 |
| 13 | 15.6 | 75 | 95 | 100 | 100 | 75 | 95 |
| 14 | 7.8 | 65 | 90 | 80 | 65 | 65 | 70 |
| 15 | 31.3 | 95 | 95 | 100 | 95 | 30 | 80 |
| 16 | 31.3 | 75 | — | 100 | 100 | 75 | 85 |
| 17 | 125 | 70 | 80 | 85 | 90 | 60 | 70 |
| 18 | 125 | 40 | 85 | 90 | 90 | 70 | 85 |
| 19 | 31.3 | 60 | 100 | 100 | 100 | 70 | 50 |
| 20 | 15.6 | 65 | 95 | 100 | 95 | 95 | 90 |
| 21 | 62.5 | 80 | 95 | 100 | 100 | 70 | 90 |
| 22 | 125 | 40 | 70 | 100 | 30 | 60 | 70 |
| 23 | 125 | 90 | 40 | 100 | 100 | 50 | 70 |
| 24 | 62.5 | 60 | 30 | 90 | 100 | 60 | 70 |
| 25 | 125 | 85 | 10 | 100 | 100 | 30 | 30 |
| 26 | 31.3 | 80 | 95 | 100 | 100 | 45 | 55 |
| 27 | 31.3 | 80 | 95 | 100 | 100 | 70 | 75 |
| 28 | 15.6 | 65 | 80 | 75 | 75 | 40 | 20 |
| 29 | 31.3 | 75 | 90 | 85 | 100 | 75 | 75 |
| 30 | 125 | 50 | 70 | 100 | 100 | 50 | 40 |
| 31 | 15.6 | 70 | 95 | 100 | 100 | 60 | 80 |
| 32 | 31.3 | 75 | 90 | 100 | 95 | 65 | 80 |
| 33 | 31.3 | 85 | 95 | 100 | 100 | 70 | 70 |
| 34 | 31.3 | 80 | 95 | 100 | 100 | 80 | 60 |
| 35 | 125 | 70 | 85 | 90 | 100 | 60 | 50 |
| 36 | 15.6 | 75 | 95 | 100 | 100 | 75 | 75 |
| 37 | 15.6 | 70 | 80 | 100 | 75 | 50 | 55 |
| 38 | 31.3 | 75 | 100 | 100 | 70 | 25 | 45 |

TABLE 3-continued

POSTMERGENCE HERBICIDAL ACTIVITY

| | | | | | | | |
|---|---|---|---|---|---|---|---|
| 39 | 125 | 60 | 80 | 90 | 100 | 50 | 70 |
| 40 | 62.5 | 70 | 90 | 95 | 100 | 40 | 30 |
| 41 | 62.5 | 60 | 60 | 90 | 100 | 50 | 50 |
| 42 | 125 | 60 | 70 | 100 | 100 | 50 | 50 |
| 43 | 62.5 | 40 | 80 | 90 | 100 | 30 | 70 |
| 44 | 125 | 70 | 40 | 100 | 100 | 50 | 70 |
| 45 | 125 | 50 | 70 | 100 | 100 | 50 | 40 |
| 46 | 60 | 60 | 90 | 100 | 50 | 50 | 100 |
| 47 | 31.3 | 70 | 95 | 100 | 100 | 55 | 80 |
| 48 | 7.8 | 75 | 90 | 100 | 100 | 65 | 40 |
| 49 | 15.6 | 75 | 95 | 100 | 100 | 75 | 75 |
| 50 | 62.5 | 65 | 95 | 95 | 100 | 65 | 70 |
| 51 | 125 | 70 | 60 | 100 | 100 | 50 | 70 |
| 52 | 62.5 | 80 | 95 | 100 | 100 | 40 | 80 |
| 53 | 31.3 | 75 | 90 | 100 | 100 | 65 | 70 |
| 54 | 31.3 | 70 | 95 | 100 | 100 | 60 | 30 |
| 55 | 15.6 | 70 | 95 | 100 | 80 | 30 | 65 |
| 56 | 15.6 | 75 | 90 | 85 | 100 | 60 | 25 |
| 57 | 62.5 | 60 | 80 | 100 | 100 | 50 | 60 |
| 58 | 62.5 | 80 | 60 | 100 | 70 | 80 | 70 |
| 59 | 15.6 | 75 | 80 | 100 | 100 | 40 | 80 |
| 60 | 31.3 | 70 | 80 | 80 | 100 | 20 | 20 |
| 61 | 125 | 70 | 95 | 100 | 100 | 55 | 40 |
| 62 | 62.5 | 85 | 90 | 100 | 100 | 70 | 80 |
| 63 | 125 | 70 | 70 | 90 | 70 | 70 | 70 |
| 64 | 31.3 | 80 | 95 | 100 | 95 | 50 | 50 |
| 65 | 125 | 70 | 70 | 90 | 40 | 70 | 40 |
| 66 | 125 | 50 | 15 | 100 | 100 | 50 | 30 |
| 67 | 62.5 | 50 | 85 | 90 | 100 | 60 | 60 |
| 68 | 31.3 | 75 | 100 | 100 | 80 | 90 | 70 |

| Cpd. No. | BWWPT | GWBLG | GWBRN | GWCRB | GWGFT | GWROX | GWWOT |
|---|---|---|---|---|---|---|---|
| 1 | 60 | 70 | 98 | 75 | 100 | 100 | 98 |
| 2 | 55 | 90 | 98 | 85 | 90 | 95 | 98 |
| 3 | 80 | 85 | 90 | 40 | 100 | 98 | 20 |
| 4 | 85 | 98 | 90 | 80 | 93 | 98 | 95 |
| 5 | 90 | 75 | 100 | 65 | — | 95 | 95 |
| 6 | 100 | 15 | 95 | 75 | — | 95 | 80 |
| 7 | 75 | 80 | 95 | 75 | 100 | 100 | 75 |
| 8 | 100 | 40 | 98 | 95 | 100 | 100 | 65 |
| 9 | 100 | 80 | 80 | 70 | 70 | 100 | 70 |
| 10 | 85 | 65 | 95 | 75 | 100 | 100 | 90 |
| 11 | 95 | 70 | 85 | 65 | 80 | 100 | 95 |
| 12 | 80 | 70 | 75 | 80 | 100 | 95 | 80 |
| 13 | 90 | 80 | 100 | 80 | 100 | 100 | 100 |
| 14 | 75 | 75 | 95 | 70 | 100 | 75 | 95 |
| 15 | 100 | 40 | 75 | 75 | 80 | 75 | 85 |
| 16 | 85 | 75 | 80 | 80 | 100 | 100 | 100 |
| 17 | 60 | 50 | 85 | 80 | 90 | 90 | 75 |
| 18 | 70 | 60 | 95 | 80 | 85 | 100 | 80 |
| 19 | 80 | 75 | 70 | 75 | 80 | 100 | 100 |
| 20 | 95 | 80 | 95 | 80 | 100 | 100 | 95 |
| 21 | 95 | 40 | 95 | 60 | 80 | 95 | 70 |
| 22 | 50 | 50 | 90 | 80 | 90 | 90 | 85 |
| 23 | 50 | 10 | 70 | 10 | 10 | 100 | 10 |
| 24 | 30 | 100 | 90 | 60 | 80 | 100 | 100 |
| 25 | 30 | 10 | 70 | 10 | 70 | 20 | 10 |
| 26 | 90 | 75 | 85 | 60 | 100 | 100 | 100 |
| 27 | 95 | 30 | 90 | 70 | 100 | 75 | 55 |
| 28 | 70 | 80 | 95 | 100 | 100 | 100 | 80 |
| 29 | 90 | 45 | 85 | 65 | 75 | 90 | 70 |
| 30 | 80 | 30 | 85 | 30 | 70 | 80 | 40 |
| 31 | 90 | 20 | 95 | 55 | 70 | 95 | 40 |
| 32 | 90 | 20 | 75 | 70 | 70 | 90 | 30 |
| 33 | 90 | 65 | 100 | 80 | 95 | 100 | 85 |
| 34 | 85 | 15 | 90 | 70 | 75 | 75 | 40 |
| 35 | 90 | 80 | 100 | 80 | 90 | 100 | 95 |
| 36 | 75 | 85 | 100 | 85 | 100 | 100 | 100 |
| 37 | 80 | 80 | 95 | 80 | 100 | 100 | 100 |
| 38 | 55 | 95 | 100 | 85 | 100 | 100 | 100 |
| 39 | 100 | 60 | 100 | 90 | 90 | 100 | 90 |
| 40 | 50 | 85 | 70 | 85 | 80 | 100 | 100 |
| 41 | 90 | 10 | 100 | 60 | 90 | 100 | 70 |
| 42 | 70 | 10 | 90 | 30 | 100 | 100 | 50 |
| 43 | 70 | 30 | 90 | 90 | 100 | 100 | 80 |

TABLE 3-continued

POSTMERGENCE HERBICIDAL ACTIVITY

| | | | | | | | |
|---|---|---|---|---|---|---|---|
| 44 | 90 | 50 | 90 | 50 | 90 | 100 | 70 |
| 45 | 70 | 90 | 90 | 80 | 90 | 100 | 100 |
| 46 | 40 | 40 | 60 | 90 | 100 | 100 | 90 |
| 47 | 95 | 55 | 90 | 70 | 85 | 85 | 45 |
| 48 | 80 | 70 | 95 | 65 | 100 | 100 | 70 |
| 49 | 80 | 80 | 100 | 85 | 80 | 95 | 95 |
| 50 | 80 | 0 | 90 | 75 | 90 | 90 | 65 |
| 51 | 50 | 15 | 100 | 15 | 90 | 100 | 50 |
| 52 | 100 | 45 | 100 | 75 | 100 | 100 | 75 |
| 53 | 80 | 80 | 95 | 70 | 95 | 100 | 70 |
| 54 | 90 | 70 | 90 | 70 | 80 | 100 | 60 |
| 55 | 75 | 40 | 75 | 90 | 75 | 100 | 85 |
| 56 | 80 | 75 | 95 | 80 | 100 | 100 | 90 |
| 57 | 80 | 50 | 70 | 70 | 70 | 100 | 70 |
| 58 | 40 | 60 | 85 | 70 | 90 | 100 | 85 |
| 59 | 75 | 0 | 60 | 55 | 75 | 100 | 55 |
| 60 | 75 | 55 | 95 | 70 | 85 | 75 | 85 |
| 61 | 90 | 40 | 85 | 55 | 70 | 65 | 65 |
| 62 | 95 | 70 | 90 | 100 | 100 | 90 | 85 |
| 63 | 80 | 80 | 80 | 85 | 90 | 100 | 90 |
| 64 | 80 | 0 | 80 | 55 | 70 | 75 | 10 |
| 65 | 70 | 85 | 90 | 40 | 90 | 100 | 85 |
| 66 | 40 | 60 | 90 | 10 | 90 | 90 | 30 |
| 67 | 50 | 90 | 90 | 30 | 90 | 70 | 100 |
| 68 | 75 | 60 | 90 | 80 | 100 | 100 | 80 |

BWCHK = chickweed (*Stellaria media*)
BWCKB = cocklebur (*Xanthium strumarium*)
BWLMQ = lambsquarters (*Chenopodium album*)
BWPIG = pigweed (*Amaranthus retroflexus*)
BWVIO = field pansy (*Viola tricolor*)
BWWBK = wild buckwheat (*Polygonum convolvulus*)
BWWPT = wild poinsettia (*Euphorbia heterophylla*)
GWBLG = blackgrass (*Alopecurus myosuroides*)
GWBRN = barnyardgrass (*Echinochloa crus-galli*)
GWCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

16. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 4.

TABLE 4

PREEMERGENCE HERBICIDAL ACTIVITY

| Cpd. No. | Rate, Kg/Ha | BWCKB | BWLMQ | BWPIG | BWVEL | BWWPT | GWBLG | GWBRN | GWCRB | GWGFT | GWROX | GWWOT |
|---|---|---|---|---|---|---|---|---|---|---|---|---|
| 5  | 0.07  | 40  | 100 | 100 | 100 | 25  | 50  | 70  | 100 | 75  | 100 | 40  |
| 6  | 0.28  | 80  | 100 | 100 | 100 | 40  | 25  | 20  | 100 | 55  | 100 | 40  |
| 8  | 0.14  | 75  | 100 | 100 | 100 | 60  | —   | 5   | 70  | —   | 100 | 15  |
| 9  | 0.14  | 70  | 100 | 100 | 100 | 55  | —   | 15  | 70  | —   | 100 | 15  |
| 10 | 0.14  | 100 | 100 | 100 | 100 | 30  | —   | 70  | 80  | 50  | 100 | 80  |
| 11 | 0.14  | 65  | 100 | 90  | 98  | 95  | —   | 15  | 100 | 60  | 98  | 75  |
| 12 | 0.28  | —   | 100 | 100 | 100 | 60  | 100 | 45  | 100 | 70  | 65  | 0   |
| 13 | 0.07  | —   | 100 | 100 | 100 | 60  | 10  | 85  | 70  | 85  | 100 | 40  |
| 14 | 0.14  | —   | 100 | 70  | 55  | 40  | 100 | 100 | 100 | 85  | 70  | 80  |
| 15 | 0.14  | —   | 100 | 100 | 100 | 65  | 0   | 80  | 100 | 95  | 100 | 65  |
| 16 | 0.14  | 100 | 100 | 100 | 100 | 60  | 30  | 30  | 100 | 60  | 100 | 65  |
| 17 | 0.07  | 50  | 100 | 100 | 80  | 50  | 0   | 85  | 100 | 100 | 75  | 35  |
| 18 | 0.28  | 100 | 100 | 100 | 100 | 100 | 50  | 95  | 100 | 65  | 100 | 100 |
| 19 | 0.28  | 90  | 100 | 100 | 100 | 80  | 30  | 20  | 100 | 100 | 90  | 90  |
| 20 | 0.28  | 90  | 100 | 100 | 100 | 100 | 30  | 80  | 100 | 40  | 80  | 90  |
| 21 | 0.14  | 55  | 100 | 0   | 25  | 25  | 20  | 45  | 100 | 100 | 100 | 30  |
| 23 | 0.28  | 90  | 100 | 100 | 75  | 65  | 60  | 0   | 70  | 45  | 70  | 0   |
| 24 | 0.035 | 45  | 100 | 100 | 100 | 50  | 30  | 55  | 100 | 100 | 75  | 70  |
| 25 | 0.28  | 100 | 100 | 100 | 100 | 95  | 0   | 30  | 60  | 70  | 60  | 0   |
| 29 | 0.28  | 100 | 100 | 100 | 100 | 50  | 55  | 25  | 75  | 85  | 30  | 40  |
| 30 | 0.28  | 100 | 100 | 100 | 50  | 30  | 30  | 60  | 100 | 100 | 65  | 0   |
| 31 | 0.28  | 100 | 100 | 100 | 80  | 85  | 25  | 70  | 70  | 100 | 100 | 30  |
| 32 | 0.28  | 50  | 100 | 50  | 30  | 20  | 0   | 10  | 50  | 10  | 20  | 20  |
| 33 | 0.28  | 30  | 100 | 100 | 20  | 50  | 10  | 20  | 100 | 100 | 90  | 90  |
| 34 | 0.28  | 100 | 100 | 100 | 65  | 50  | 20  | 60  | 70  | 0   | 80  | 40  |
| 35 | 0.14  | 30  | 65  | 100 | 60  | 20  | 40  | 30  | 100 | 100 | 100 | 40  |
| 41 | 0.28  | 100 | 100 | 100 | 45  | 70  | 0   | 0   | 80  | 35  | 100 | 30  |
| 42 | 0.28  | 80  | 100 | 70  | 40  | 40  | 0   | 0   | 100 | 75  | 100 | 0   |
| 43 | 0.28  | 55  | 100 | 100 | 50  | 40  | 60  | 0   | 60  | 100 | 100 | 50  |
| 44 | 0.14  | 40  | 100 | 100 | 100 | 20  | 20  | 25  | 100 | 100 | 100 | 40  |
| 45 | 0.28  | 40  | 100 | 100 | 85  | 0   | 45  | 0   | 100 | 100 | 100 | 85  |
| 46 | 0.14  | 30  | 100 | 100 | 100 | 25  | 30  | 25  | 100 | 100 | 100 | 15  |
| 48 | 0.07  | 25  | 100 | 100 | 100 | 65  | 50  | 70  | 100 | 100 | 100 | 20  |
| 49 | 0.14  | 70  | 100 | 100 | 100 | 70  | 50  | 100 | 100 | 100 | 90  | 70  |
| 50 | 0.28  | 20  | 100 | 100 | 40  | 20  | 0   | 0   | 10  | 78  | 10  | 10  |
| 51 | 0.14  | 100 | 100 | 80  | 100 | 20  | 40  | 0   | 60  | 50  | 100 | 40  |
| 53 | 0.56  | 100 | 100 | 100 | 100 | 50  | 80  | 95  | 100 | 100 | 95  | 80  |
| 54 | 0.56  | 20  | 10  | 100 | 100 | 100 | 20  | 20  | 100 | 10  | 100 | 10  |
| 55 | 0.28  | 30  | 100 | 100 | 100 | 50  | 0   | 90  | 100 | 100 | 100 | 50  |
| 56 | 0.28  | 10  | 100 | 100 | 100 | 20  | 10  | 30  | 100 | 100 | 90  | 30  |
| 57 | 0.07  | 40  | 75  | 100 | 100 | 10  | 15  | 100 | 100 | 100 | 100 | 20  |
| 58 | 0.28  | 95  | 100 | 75  | 100 | 30  | 35  | 100 | 100 | 100 | 100 | 50  |
| 66 | 0.14  | 100 | 100 | 100 | 100 | 55  | 30  | 10  | 80  | 55  | 100 | 60  |
| 67 | 0.14  | 100 | 100 | 100 | 100 | 45  | 80  | 60  | 100 | 100 | 100 | 100 |

BWCKB = cocklebur (*Xanthium strumarium*)
BWLMQ = lambsquarters (*Chenopodium album*)
BWMGL = morningglory (*Ipomoea hederacea*)
BWPIG = pigweed (*Amaranthus retroflexus*)
BWVEL = velvetleaf (*Abutilion theophrasti*)
BWWPT = wild poinsettia (*Euphorbia heterophylla*)
GWBLG = blackgrass (*Alopecurus myosuroides*)
GWBRN = barnyardgrass (*Echinochloa crus-galli*)
GBCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

What is claimed is:

1. A benzoic acid compound of the formula:

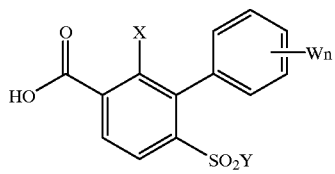

wherein
X represents F, Cl, Br, $CH_3$, $C_2H_5$, or $OCH_3$;
Y represents $CH_3$, $C_2H_5$, $CH(CH_3)_2$, or cyclo-$C_3H_5$;
W represents F, Cl, Br, CN, $NO_2$, OH, R", OR", OCOR", OCONHR", $OSO_2R$", SR", SOR", $SO_2R$", $SO_2OR$", $SO_2NHR$", $SO_2NR"_2$, NHR", $NR"_2$, $CO_2R$", CONHR", or $CONR"_2$; or any two adjacent W together represent the fragment —$O(CH_2)_mO$— optionally mono to completely substituted with fluorine or methyl;
n represents 0, 1, 2, or 3;
m represents 1, 2, or 3; and R" represents $C_1$–$C_4$ alkyl, $C_2$–$C_4$ alkenyl, or $C_2$–$C_4$ alkynyl each optionally mono to completely substituted with fluorine or mono substituted with Cl, Br, O($C_1$–$C_2$ alkyl), or S($C_1$–$C_2$ alkyl).

2. A compound according to claim 1 wherein X represents methyl.

3. A compound according to claim 1 wherein Y represents methyl.

4. A compound according to claim 1 wherein W represents fluoro, chloro, methyl, ethyl, hydroxy, methoxy, ethoxy, 1-methylethoxy, 2-propenyloxy, or methoxymethoxy.

5. A compound according to claim 1 wherein n represents 1 and the substituent is located in the 4-position.

6. A compound according to claim 1 wherein W represents methoxy, ethoxy, 1-methylethoxy, or methoxy-methoxy.

7. A compound according to claim 1 selected from 2-methyl-4-methylsulfonyl-3-(4-methoxyphenyl)benzoic acid, 2-methyl-4-methylsulfonyl-3-(4-ethoxyphenyl) benzoic acid, and 2-methyl-4-methylsulfonyl-3-(4-methoxymethoxy-phenyl)benzoic acid.

* * * * *